United States Patent
Wang et al.

(10) Patent No.: US 6,881,314 B1
(45) Date of Patent: Apr. 19, 2005

(54) APPARATUSES AND METHODS FOR FIELD FLOW FRACTIONATION OF PARTICLES USING ACOUSTIC AND OTHER FORCES

(75) Inventors: Xiao-Bo Wang, San Diego, CA (US); Jing Cheng, Beijing (CN); Lei Wu, San Diego, CA (US); Junquan Xu, Fujian (CN)

(73) Assignee: Aviva Biosciences Corporation, San Diego, CA (US)

( * ) Notice: Subject to any disclaimer, the term of this patent is extended or adjusted under 35 U.S.C. 154(b) by 454 days.

(21) Appl. No.: 09/679,023

(22) Filed: Oct. 4, 2000

(30) Foreign Application Priority Data

Sep. 30, 2000 (CN) .......................................... 12000724

(51) Int. Cl.$^7$ .......................... C02F 1/40; C25B 11/00; C25B 13/00; C25B 9/00; G01N 27/27
(52) U.S. Cl. ........................ 204/600; 204/450; 204/547
(58) Field of Search ................................ 204/600, 450, 204/547

(56) References Cited

U.S. PATENT DOCUMENTS

| | | | |
|---|---|---|---|
| 3,449,938 A | 6/1969 | Giddings ........................ 73/23 |
| 4,523,682 A | 6/1985 | Barmatz et al. ............. 209/638 |
| 4,743,361 A | 5/1988 | Schram ......................... 209/1 |
| 4,832,814 A | * 5/1989 | Root ....................... 435/285.2 |
| 4,874,507 A | * 10/1989 | Whitlock ..................... 209/11 |
| 4,877,516 A | 10/1989 | Schram ...................... 209/155 |
| 5,192,450 A | 3/1993 | Heyman ..................... 210/748 |
| 5,240,618 A | 8/1993 | Caldwell et al. ............ 210/748 |
| 5,245,290 A | * 9/1993 | Cannon et al. ............. 324/457 |
| 5,302,898 A | 4/1994 | Pethig et al. ................ 324/316 |
| 5,683,859 A | 11/1997 | Nothnagle et al. .......... 430/488 |
| 5,795,457 A | 8/1998 | Pethig et al. ................ 204/547 |
| 5,800,690 A | 9/1998 | Chow et al. ................. 204/451 |
| 5,811,658 A | 9/1998 | Van Driel .................. 73/19.02 |
| 5,814,200 A | 9/1998 | Pethig et al. ................ 204/547 |
| 5,846,708 A | * 12/1998 | Hollis et al. .................... 435/6 |
| 5,888,370 A | * 3/1999 | Becker et al. .............. 204/643 |
| 5,993,630 A | * 11/1999 | Becker et al. .............. 204/547 |
| 5,993,631 A | 11/1999 | Parton et al. ............... 204/547 |
| 5,993,632 A | 11/1999 | Becker et al. .............. 204/547 |
| 6,071,394 A | 6/2000 | Cheng et al. ............... 204/547 |
| 6,216,538 B1 | * 4/2001 | Yasuda et al. ............. 73/570.5 |
| 6,246,046 B1 | * 6/2001 | Landers et al. ............. 250/216 |
| 6,294,063 B1 | * 9/2001 | Becker et al. .............. 204/450 |
| 6,372,506 B1 | * 4/2002 | Norton ........................ 436/63 |

FOREIGN PATENT DOCUMENTS

| | | |
|---|---|---|
| EP | 0292470 | 11/1988 |
| EP | 0302724 | 2/1989 |
| GB | 2166659 | 5/1986 |
| WO | WO 93/16383 | 8/1993 |
| WO | WO 96/07917 | 3/1996 |
| WO | WO 97/27933 | 8/1997 |
| WO | WO 97/34689 | 9/1997 |
| WO | WO 98/04355 | 2/1998 |
| WO | WO 99/12016 | 3/1999 |

(Continued)

OTHER PUBLICATIONS

U.S. Appl. No. 09/679,024, filed Oct. 4, 2000, Wang et al.
Caldwell and Gao, Anal. Chem. (1993) 65:1764–1772.
Giddings, Anal. Chem. (1981) 53:1170A–1178A.

(Continued)

Primary Examiner—Mark L. Bell
Assistant Examiner—Jennine Brown
(74) Attorney, Agent, or Firm—Morrison & Foerster LLP

(57) ABSTRACT

This invention relates generally to the field of field-flow-fractionation. In particular, the invention provides apparatuses and methods for the discrimination of matters utilizing acoustic force, or utilizing acoustic force with electrophoretic or dielectrophoretic force, in field flow fractionation.

34 Claims, 10 Drawing Sheets

FOREIGN PATENT DOCUMENTS

| | | |
|---|---|---|
| WO | WO 00/32744 | 6/2000 |
| WO | WO 00/37163 | 6/2000 |
| WO | WO 00/47322 | 8/2000 |
| WO | WO 01/05511 | 1/2001 |
| WO | WO 01/05512 | 1/2001 |
| WO | WO 01/05513 | 1/2001 |
| WO | WO 01/05514 | 1/2001 |

OTHER PUBLICATIONS

Giddings, Science (1993) 260:1456–1465.
Huang et al., Biophys. J. (1997) 73:1118–1129.
Huang et al., J. Hematotherapy and Stem Cell Research (1999) 8:481–490.
Lee et al., Anal. Chem. (1989) 61:2439–2444.
Levin and Giddings, J. Chem. Tech. Biotechnol. (1991) 50:43–56.
Markx et al., J. Liq. Chrom. & Rel. Technol. (1997) 20:2857–2872.
Pui et al., Biotechnol. Prog. (1995) 11:146–152.
Ratanathanawongs and Giddings, Anal. Chem. (1992) 64:6–15.
Springston et al., Anal Chem. (1987) 59:344–350.
Wang et al., Biophys. J. (1998) 74:2689–2701.
Williams et al., Chem. Eng. Comm. (1992) 111:121–147.
Williams et al., Chem. Eng. Comm. (1994) 130:143–166.
Williams et al., Chem. Eng. Sci. (1996) 51:4477–4488.
Williams et al., Anal. Chem. (1997) 69:349–360.
Yang et al., Anal. Chem. (1999) 71:911–918.
Yasuda et al., J. Acoust. Soc. Am. (1996A) 99(4):1965–1970.
Yasuda et al., Jpn. J. Appl. Phys. (1996B) 35(1), No. 5B:3295–3299.
Yasuda et al., J. Acoust. Soc. Am. (1996C) 99(2):1248–1251.
Yasuda et al., J. Acoust. Soc. Am. (1997) 102(1):642–645.
Yasuda and Kamakura, Appl. Phys. Lett. (1997) 71:1771–1773.
Yosioka and Kawashima, Acustica (1955) 5:167–173.
Curtis, H. W., et al., "Ultrasonic Continuous Flow Plasmapheresis Separator" IBM Technical Disclosure Bulletin 25(1):192–193 (1982).
Green, N. G., et al., "Separation of Submicrometre Particles Using a Combination of Dielectrophoretic and Electrohydrodynamic Forces" Journal of Physics 31(7):L25–L30 (1998).

* cited by examiner (A)

(B)

(A)

(B)

APPARATUSES AND METHODS FOR FIELD FLOW FRACTIONATION OF PARTICLES USING ACOUSTIC AND OTHER FORCES

RELATED APPLICATION

This application is related to a first Chinese national patent application TW536,423, filed Sep. 30, 2000, entitled "APPARATUSES AND METHODS FOR FIELD-FLOW—FRACTIONATION OF PARTICLES USING ACOUSTIC AND OTHER FORCES," a second Chinese national patent application TW593,683, filed Sep. 30, 2000, entitled "APPARATUSES CONTAINING MULTIPLE FORCE GENERATING ELEMENTS AND USES THEREOF," and an U.S. patent application Ser. No. 09/679,024, filed Oct. 4, 2000, entitled "APPARATUSES CONTAINING MULTIPLE FORCE GENERATING ELEMENTS AND USES THEREOF." The disclosure of the above referenced patent applications is incorporated by reference in their entirety.

TECHNICAL FIELD

This invention relates generally to the field of field-flow-fractionation. In particular, the invention provides apparatuses and methods for the discrimination of matters utilizing acoustic force, or utilizing acoustic force with electrophoretic or dielectrophoretic force, in field flow fractionation.

BACKGROUND ART

Electrical-field-flow-fractionation (E-FFF) and dielectrophoretic-field-flow-fractionation (DEP-FFF) are known in the art. For example, U.S. Pat. No. 5,240,618 discloses an electrical field-flow-fractionation method, and U.S. Pat. Nos. 5,888,370, 5,993,630 and 5,993,632 disclose methods and apparatuses for fractionation using conventional and generalized dielectrophoresis and field flow fractionation. In E-FFF (Caldwell and Gao, 1993), electrophoretic forces are used to balance sedimentation forces (for large particle application, particle size being several micron or larger) and/or diffusion forces (for small particle application) and to control particle equilibrium positions (or equilibrium distribution profile) in a fluid flow velocity profile. Particles of different charges or sizes or densities exhibit different equilibrium positions (or different distribution profiles), and are caused to move through the chamber at different velocities, and can thus be separated into different fractionations. In DEP-FFF (Huang et al, 1997, Markx et al, 1997, Wang et al, 1998), DEP force components in the vertical direction are used to balance sedimentation forces and control particle equilibrium positions in a fluid flow profile. Particles of different dielectric properties are positioned at different heights in the flow profile and are thereby transported at different velocities. A particle mixture introduced into an E-FFF or DEP-FFF chamber can be fractionated into sub-populations according to the time they exit the chamber. E-FFF separation has been demonstrated on colloidal adsorption complexes. DEP-FFF separation has been demonstrated on synthetic polystyrene beads and biological cells.

However, the currently available apparatuses and methods used in field-flow-fractionation suffer from the following limitations. For E-FFF, electrode polarization presents a significant problem since majority of the applied voltage is dropped across the electrode/medium interface. Furthermore, electrical charge may be used as a separation or fractionation parameter for only certain cases. Similarly, for DEP-FFF, dielectric properties may be used as separation bases for only certain problems. Positive DEP force has not been exploited for particle DEP-FFF separation. The separation efficiency using current field-flow-fractionation methods is still not satisfactory for many application problems. Thus, there is a need to further improve field-flow-fractionation methods so that the methods have improved applicability and separation efficiency to many separation problems. The present invention addresses these and other related needs in the art.

DISCLOSURE OF THE INVENTION

This invention provides apparatuses and methods for particle characterization, manipulation and separation using acoustic radiation force (or acoustic force), electrophoretic (E) force, dielectrophoretic (DEP) force, gravitational force, hydrodynamic force and a fluid flow profile. A new force component, i.e., acoustic-radiation-force, is introduced to the techniques of field-flow-fractionation (FFF), electrical-field-flow-fractionation (E-FFF), dielectrophoretic-field-flow-fractionation (DEP-FFF), and thus the present invention has a number of advantages over current FFF or E-FFF or DEP-FFF apparatuses and methods:

Particles, e.g., cells, can be separated according to their properties such as size, density, dielectric parameters, electrical charges, as well as their acoustic impedance—a new parameter for particle discrimination and separation.

Positive DEP forces may also be exploited for particle separation—a new dimension to the DEP-FFF method where only negative DEP forces are used.

Better particle separation efficiency can be achieved.

Since an acoustic radiation force (or for simplicity, acoustic force) is used as an additional force component to influence particle positions including particle equilibrium positions, or particle distribution profiles including particle equilibrium distribution profiles, in FFF or E-FFF or DEP-FFF operation, the methods are termed acoustic-FFF or acoustic-E-FFF or acoustic-DEP-FFF. Particles refer to any matter, particular matter, or solubilized matter, or any combination thereof. The acoustic force is produced by establishing an acoustic wave, e.g., an acoustic standing wave, in the chamber in the direction normal to that of the fluid flow and parallel to the active DEP force components or electrophoretic force components. The acoustic standing waves can be generated using any methods known in the art, e.g., using piezoelectric transducers.

The present invention provides methods and apparatuses for the discrimination of particulate matter and solubilized matter of different types. This discrimination may include, for example, separation, characterization, differentiation and manipulation of the particulate matter. According to the present invention, the particulate matter may be placed in liquid suspension before input into the apparatus. The discrimination occurs in the apparatus, which may be a thin, enclosed chamber. Particles may be distinguished, for example, by differences in their density, size, dielectric permitivity, electrical conductivity, surface charge, surface configuration, and/or acoustic impedance. The apparatuses and methods of the present invention may be used to discriminate different types of matter simultaneously.

The apparatuses and methods are applicable to the characterization, manipulation and separation of many types of particles—solid particles such as glass beads, latex particles, liquid particles such as liquid droplets, or gaseous particles such as gas bubble. Particles can be organic ones, e.g., mammalian cells, bacteria, virus, or other microorganisms, or inorganic ones, e.g., metal particles. Particles can be of different shapes, e.g., sphere, elliptical sphere, cubic, discoid, needle-type, and can be of different sizes, e.g., nano-meter-size gold sphere, to micrometer-size cells, to millimeter-size particle-aggregate. Examples of particles include, but not limited to, biomolecules such as DNA, RNA, chromosomes, protein molecules, e.g., antibodies, cells, colloid particles, e.g., polystyrene beads.

The apparatuses and methods are applicable to any particle separation problems, in particular cell separations in biomedical setting. Examples of particle separation include, but not limited to, separation of cancer cells from normal cells, metastatic cancer cells from blood, fetal nucleated cells from maternal erythrocytes/nucleated cells, virus-infected cells from normal counterpart cells, red blood cells from white blood cells, bacteria from blood or urine or other body fluid, etc. For biological applications using living cells, the present invention allows cells to be separated without the need to alter them with ligands, stains, antibodies or other means. Non-biological applications similarly require no such alteration. It is recognized however, that the apparatuses and methods according to the present invention are equally suitable for separating such biological matter even if they have been so altered. The separation process in the present invention introduces little or non-stress on the matter to be separated. Living cells remain undamaged, unaltered and viable during and following separation using the present invention. Or, the stress on the cells is small enough so that the separated cells are still applicable for further characterization, assay or analysis, or growth following separation using the present invention.

A. Apparatuses using Acoustic Forces (Acoustic-FFF Apparatuses)

In one aspect, the present invention provides an apparatus for the discrimination of a matter utilizing acoustic forces in field flow fractionation, which apparatus comprises: a) a chamber having at least one inlet port and at least one outlet port, said chamber having such structural characteristics that when a carried medium is caused to travel through said chamber, the traveling velocity of said carried medium at various positions within said chamber is different; (b) at least one piezoelectric transducer adapted along a portion of said chamber, wherein said piezoelectric transducer can be energized via at least one electrical signal provided by an electrical signal generator to create an acoustic wave, thereby causing at least one acoustic force having components normal to the traveling direction of said carrier medium on a matter in said carrier medium.

The apparatus can have a single inlet port and a single outlet port. Alternatively, the apparatus can have a plurality of inlet and/or outlet ports. Preferably, the outlet port is connected to a collection device or a characterization device. The outlet port of the chamber according to the present invention may take many forms. Specifically, the outlet port may be a single port, or a plurality of ports, or an array of ports. The outlet port, for example, may be located along the entire width or a part of the width of the chamber. The outlet port may be adapted to receive matter of various shapes and sizes. For example, the size of the outlet port may vary from approximately twice the size of the matter to be discriminated to the entire width of the chamber. In one embodiment, the outlet port may be constructed of one or more tubing elements, such as TEFLON tubing. The tubing elements may be combined to provide an outlet port. Further, for example, the outlet port may be connected to fraction collectors or collection wells that are used to collect separated matter. Other components that may be connected to the apparatus of the present invention are, for example, measurement or diagnostic equipment, such as cytometers, particle counters and spectrometers. Other devices or apparatus used for further assay or analyses on the separated matters may also be connected to the apparatus of the present invention.

The chamber of the apparatus should be designed to have such structural characteristics that when a fluid (liquid or gas) is caused to travel through the chamber, the velocity of the fluid (liquid or gas) at various positions within said chamber is different and the fluid (liquid or gas) travels through the chamber according to a velocity profile. For example, the chamber may be rectangular in shape and may include, for example, a top wall, a bottom wall and two side walls. The top wall and bottom wall may be parallel to each other, or substantially parallel to each other, and the distance between the top wall and the bottom is referred to as chamber height. The distance between the inlet port and outlet port is referred to as chamber length when the chamber comprises one inlet port and one outlet port. The two side walls may be parallel to each other, or substantially parallel to each other, and the distance between the two side walls of the chamber that are parallel to each other is referred to as chamber width. The two side walls may be parts of a gasket or a spacer between the top wall and bottom wall. The gasket or spacer may be cut in the middle to form a rectangular thin channel with taper ends. Alternatively, the gasket or spacer may be cut in the middle to form thin channels of other shapes such as ellipse, circle, or any other shape. In certain embodiments, the chamber may be constructed so that the top wall and bottom wall are of a much greater magnitude than the side walls (e.g., both chamber length and chamber width are substantially greater than the chamber height for a chamber with a rectangular shape), thereby creating a thin chamber. For such a thin chamber having a rectangular channel in the middle, when a carrier medium is caused to travel through the thin rectangular channel (or called "travel through the chamber"), the velocity of the carrier medium in the chamber may follow a parabolic or a near-parabolic profile. The velocity of the carrier medium at the top and bottom walls is zero, and with increasing the distances from the top wall or from the bottom wall, the velocity of the carrier medium increases to a maximum value at the middle position between the top and bottom walls. In other embodiments, the chamber may be constructed so that the top wall and bottom wall are of a much smaller magnitude than the side walls (e.g., both chamber length and chamber height are substantially greater than the chamber width for a chamber with a rectangular shape), again creating a thin chamber. In addition to the rectangular shape of the chamber, the chamber may be of circular construction, elliptical, triangular, hexadecagonal, or of other geometrical shapes. The chamber may be constructed having a top wall, a bottom wall, and a gasket or a spacer between the top and bottom wall. The gasket or spacer may be cut in the middle to form rectangular thin channel with taper ends. Alternatively, the gasket or spacer may be cut in the middle to form thin channels of other shapes such as ellipse, circle, or any other shape. In the case of a thin rectangular channel where the top and bottom walls on two different planes are parallel to each other, the velocity of the carrier-medium in the chamber may follow a parabolic or a near-parabolic velocity profile. The velocity of the carrier medium at the top and bottom walls is zero, and with increasing the distances from the top wall or from the bottom wall, the velocity of the carrier medium increases to a maximum value at the middle position between the top and bottom walls. Preferably, for a rectangular channel, the width of the channel is from about 1 mm to about 20 cm, and the thickness of the channel is from about 20 micron to about 10 mm, and the length of the channel is from about 1 cm to about 200 cm, and preferably from about 10 cm to about 50 cm. As such, the present invention is not intended to be limited to a particular geometric shape and the chamber may be constructed of many different materials, for example, glass, polymeric material, plastics, quartz, coated metal, or the like, provided that the chamber has such structural characteristics that when a carrier medium is caused to travel through the chamber, the velocity of the medium at different positions in the chamber is different.

The apparatus can comprise a single piezoelectric transducer or comprise a plurality of piezoelectric transducers. The plurality of piezoelectric transducers may be energized via common electrical signals or via different electrical signals. The plurality of piezoelectric transducers can be adapted along the interior or exterior surface of the chamber. The plurality of piezoelectric transducers can also be configured on a plane substantially parallel to traveling direction of the carrier medium that is caused to travel through the chamber.

Preferably, the electrical signal generator for energizing the piezoelectric transducer to create the acoustic force is capable of varying magnitude, and frequency of said electrical signals.

In a preferred embodiment, the chamber of the apparatus comprises a tube. The piezoelectric transducer, or a plurality thereof, can be adapted along the interior surface of the tube. Alternatively, the piezoelectric transducer, or a plurality thereof, can be adapted along the exterior surface of the tube.

In another preferred embodiment, the chamber comprises a top wall, a bottom wall, and two side walls. The piezoelectric transducer, or a plurality thereof, can be configured on the top wall of the chamber. Alternatively, the piezoelectric transducer, or a plurality thereof, can be configured on the bottom wall of the chamber. In another configuration, the piezoelectric transducer, or a plurality thereof, can be adapted on opposing surfaces of the chamber. Preferably, the chamber height between the top and bottom walls is about half wavelength of the standing acoustic wave.

An apparatus for the discrimination of a matter utilizing acoustic forces in field flow fractionation is also provided, which apparatus consists essentially of, or consists of, a) a chamber having at least one inlet port and at least one outlet port, said chamber having such structural characteristics that when a carried medium is caused to travel through said chamber, the traveling velocity of said carried medium at various positions within said chamber is different; b) at least one piezoelectric transducer adapted along a portion of said chamber, wherein said piezoelectric transducer can be energized via at least one electrical signal provided by an electrical signal generator to create an acoustic wave, thereby causing at least one acoustic force having components normal to the traveling direction of said carrier medium on a matter in said carrier medium.

B. Apparatuses using Electrophoretic (E) and Acoustic Forces (Acoustic-E-FFF Apparatuses)

In another aspect, the present invention provides an apparatus for the discrimination of a matter utilizing electrophoretic and acoustic forces in field flow fractionation, which apparatus comprises: a) a chamber having at least one inlet port and at least one outlet port, said chamber having such structural characteristics that when a carried medium is caused to travel through said chamber, the traveling velocity of said carried medium at various positions within said chamber is different; b) at least two electrode elements adapted along a portion of said chamber, wherein said electrode elements can be energized via at least one electrical signal provided by an electrical signal generator to create an electrical field, thereby causing at least one electrophoretic force having components normal to the traveling direction of said carrier medium on a matter in said carrier medium; and c) at least one piezoelectric transducer adapted along a portion of said chamber, wherein said piezoelectric transducer can be energized via at least one electrical signal provided by an electrical signal generator to create an acoustic wave, thereby causing at least one acoustic force having components normal to the traveling direction of said carrier medium on a matter in said carrier medium.

The apparatus can have a single inlet port and a single outlet port. Alternatively, the apparatus can have a plurality of inlet and/or outlet ports. Preferably, the outlet port is connected to a collection device or a characterization device. The outlet port of the chamber according to the present invention may take many forms. Specifically, the outlet port may: be a single port, or a plurality of ports, or an array of ports. The outlet port, for example, may be located along the entire width or a part of the width of the chamber. The outlet port may be adapted to receive matter of various shapes and sizes. For example, the size of the outlet port may vary from approximately twice the size of the matter to be discriminated to the entire width of the chamber. In one embodiment, the outlet port may be constructed of one or more tubing elements, such as TEFLON tubing. The tubing elements may be combined to provide an outlet port. Further, for example, the outlet port may be connected to fraction collectors or collection wells that are used to collect separated matter. Other components that may be connected to the apparatus of the present invention are, for example, measurement or diagnostic equipment, such as cytometers, particle counters and spectrometers. Other devices or apparatus used for further assay or analyses on the separated matters may also be connected to the apparatus of the present invention.

The chamber of the apparatus should be designed to have such structural characteristics that when a fluid (liquid or gas) is caused to travel through the chamber, the velocity of the fluid (liquid or gas) at various positions within said chamber is different and the fluid (liquid or gas) travels through the chamber according to a velocity profile. For example, the chamber may be rectangular in shape and may include, for example, a top wall, a bottom wall and two side walls. The top wall and bottom wall may be parallel to each other, or substantially parallel to each other, and the distance between the top wall and the bottom is referred to as chamber height. The distance between the inlet port and outlet is referred to as chamber length when the chamber comprises one inlet port and one outlet port. The two side walls may be parallel to each other, or substantially parallel to each other, and the distance between the two side walls of the chamber is referred to as chamber width. The two side walls may be parts of a gasket or a spacer between the top wall and bottom wall. The gasket or spacer may be cut in the middle to form a rectangular thin channel with taper ends. Alternatively, the gasket or spacer may be cut in the middle to form thin channels of other shapes such as ellipse, circle, or any other shape. In certain embodiments, the chamber may be constructed so that the top wall and bottom wall are of a much greater magnitude than the side walls (e.g., both chamber length and chamber width are substantially greater than the chamber height for a chamber with a rectangular shape), thereby creating a thin chamber. For such a thin chamber having a rectangular channel in the middle, when a carrier medium is caused to travel through the thin rectangular channel (or called "travel through the chamber"), the velocity of the carrier medium in the chamber may follow a parabolic or a near-parabolic profile. The velocity of the carrier medium at the top and bottom walls is zero, and with increasing the distances from the top wall or from the bottom wall, the velocity of the carrier medium increases to a maximum value at the middle position between the top and bottom walls. In other embodiments, the chamber may be constructed so that the top wall and bottom wall are of a much smaller magnitude than the side walls (e.g., both chamber length and chamber height are substantially greater than the chamber width for a chamber with a rectangular shape), again creating a thin chamber. In addition to the rectangular shape of the chamber, the chamber may be of circular construction, elliptical, triangular, hexadecagonal, or of other geometrical shapes. The chamber may be constructed having a top wall, a bottom wall, and a gasket or a spacer between the top and bottom wall. The gasket or spacer may be cut in the middle to form rectangular thin channel with taper ends. Alternatively, the gasket or spacer may be cut in the middle to form thin channels of other shapes such as ellipse, circle, or any other shape. In the case of a thin rectangular channel where the top and bottom walls on two different planes are parallel to each other, the velocity of the carrier medium in the medium may follow a parabolic or a near-parabolic velocity profile. The velocity of the carrier medium at the top and bottom walls is zero, and with increasing the distances from the top wall or from the bottom wall, the velocity of the carrier medium increases to a maximum value at the middle position between the top and bottom walls. Preferably, for a rectangular channel, the width of the channel is from about 1 mm to about 20 cm, and the thickness of the channel is from about 20 micron to about 10 mm, and the length of the channel is from about 1 cm to about 200 cm, preferably from about 10 cm to about 50 cm. As such, the present invention is not intended to be limited to a particular geometric shape and the chamber may be constructed of many different materials, for example, glass, polymeric material, plastics, quartz, coated metal, or the like, provided that the chamber has such structural characteristics that when a carrier medium is caused to travel through the chamber, the velocity of the medium at different positions in the chamber is different.

The apparatus can comprise two, or more than two electrode elements. Each of the electrode elements can be individually connected to one of a plurality of electrical conductor buses electrically connected to the electrical signal generator. The electrode elements can be adapted substantially longitudinally or latitudinally along a portion of the chamber. The electrode elements can be adapted along the interior or exterior surface of the chamber. The electrode elements can be configured on a plane substantially parallel to traveling direction of the carrier medium caused to travel through said chamber. Preferably, the electrode elements configured on a plane form an electrode array. The electrode array may be an interdigitated electrode array, interdigitated castellated electrode array, interdigitated electrode array with arc-shape tip extensions. Preferably, the electrode element is a metal layer, e.g., a gold layer, coated on a surface of the chamber. Other metals such as platinum, aluminum, chromium, titanium, copper and silver may also be used.

The electrical signal generator for energizing the electrode element to create the electrophoretic force may be a DC signal source capable of varying magnitude of DC voltage, or may be an AC signal source capable of varying magnitude and frequency, of electrical signals. Preferably, the electrical signal for energizing the electrode element to create the electrophoretic force is a direct current (DC) electrical signal or a low-frequency-alternating current (AC) signal.

The apparatus can comprise a single piezoelectric transducer or comprise a plurality of piezoelectric transducers. The plurality of piezoelectric transducers may be energized via common electrical signals or via different electrical signals. The plurality of piezoelectric transducers can be adapted along the interior or exterior surface of the chamber. The plurality of piezoelectric transducers can also be configured on a plane substantially parallel to traveling direction of the carrier medium that is caused to travel through the chamber.

Preferably, the electrical signal generator for energizing the piezoelectric transducer to create the acoustic force is capable of varying magnitude and frequency of said electrical signals.

Common electrical conductor buses may be used to connect a plurality of electrode elements to the signal generator. The common electrical conductor buses may be fabricated by the same process as the fabricated electrode elements in the apparatus, or may be one or more conducting assemblies, such as a ribbon conductor, metallized ribbon or metallized plastic. For an interdigitated electrode array, alternating electrode elements along the array may be connected together so as to receive electrical signals from the signal generator. The electrical generator may be a DC voltage supply capable of generating voltages of varying magnitude. Voltage signals desired for the apparatuses and methods of the present invention are in the range of about 0 to about 15 volts, and more preferably between about 0 to about 2 volts. The signal generator may be a signal generator capable of generating signals of varying voltage and frequency and may be, for example, a function generator, such as a Hewlett Packard generator Model No. 8116A. Signals desired for the apparatuses and methods of the present invention are in the range of about 0 to about 15 volts, and about 0.1 Hz to about 100 kHz, and more preferably between about 0 to about 2 volts, and about 0.1 Hz to 1 kHz.

In a preferred embodiment, the chamber of the apparatus comprises a tube. The electrode element and/or the piezoelectric transducer, or a plurality thereof, can be adapted along the interior surface of the tube. Alternatively, the electrode element and/or the piezoelectric transducer, or a plurality thereof, can be adapted along the exterior surface of the tube.

In another preferred embodiment, the chamber comprises a top wall, a bottom wall, and two side walls. The electrode element and/or the piezoelectric transducer, or a plurality thereof, can be configured on the top wall of the chamber. Alternatively, the electrode element and/or the piezoelectric transducer, or a plurality thereof, can be configured on the bottom wall of the chamber. In another configuration, the electrode element and/or the piezoelectric transducer, or a plurality thereof, can be adapted on opposing surfaces of the chamber. Preferably, the chamber height between the top and bottom walls is about half wavelength of the standing acoustic wave.

In still another preferred embodiment, the apparatus consists essentially of, or consists of: a) a chamber having at least one inlet port and at least one outlet port, said chamber having such structural characteristics that when a carried medium is caused to travel through said chamber, the traveling velocity of said carried medium at various positions within said chamber is different; b) at least two electrode elements adapted along a portion of said chamber, wherein said electrode elements can be energized via at least one electrical signal provided by an electrical signal generator to create an electrical field, thereby causing at least one electrophoretic force having components normal to the traveling direction of said carrier medium on a matter in said carrier medium; and c) at least one piezoelectric transducer adapted along a portion of said chamber, wherein said piezoelectric transducer can be energized via at least one electrical signal provided by an electrical signal generator to create an acoustic wave, thereby causing at least one acoustic force having components normal to the traveling direction of said carrier medium on a matter in said carrier medium.

C. Apparatuses using Dielectrophoretic (DEP) and Acoustic Forces (Acoustic-DEP-FFF Apparatuses)

In another aspect, the present invention provides an apparatus for the discrimination of a matter utilizing dielectrophoretic and acoustic forces in field flow fractionation, which apparatus comprises: a) a chamber having at least one inlet port and at least one outlet port, said chamber having such structural characteristics that when a carried medium is caused to travel through said chamber, the traveling velocity of said carried medium at various positions within said chamber is different; b) at least two electrode elements adapted along a portion of said chamber, wherein said electrode elements can be energized via at least one electrical signal provided by an electrical signal generator to create a non-uniform electrical field, thereby causing at least one dielectrophoretic force having components normal to the traveling direction of said carrier medium on a matter in said carrier medium; and c) at least one piezoelectric transducer adapted along a portion of said chamber, wherein said piezoelectric transducer can be energized via at least one electrical signal provided by an electrical signal generator to create an acoustic wave, thereby causing at least one acoustic force having components normal to the traveling direction of said carrier medium on a matter in said carrier medium.

The apparatus can have a single inlet port and a single outlet port. Alternatively, the apparatus can have a plurality of inlet and/or outlet ports. Preferably, the outlet port is connected to a collection device or a characterization device. The outlet port of the chamber according to the present invention may take many forms. Specifically, the outlet port may be a single port, or a plurality of ports, or an array of ports. The outlet port, for example, may be located along the entire width or a part of the width of the chamber. The outlet port may be adapted to receive matter of various shapes and sizes. For example, the size of the outlet port may vary from approximately twice the size of the matter to be discriminated to the entire width of the chamber. In one embodiment, the outlet port may be constructed of one or more tubing elements, such as TEFLON tubing. The tubing elements may be combined to provide an outlet port. Further, for example, the outlet port may be connected to fraction collectors or collection wells that are used to collect separated matter. Other components that may be connected to the apparatus of the present invention are, for example, measurement or diagnostic equipment, such as cytometers, particle counters and spectrometers. Other devices or apparatus used for further assay or analyses on the separated matters may also be connected to the apparatus of the present invention.

The chamber of the apparatus should be designed to have such structural characteristics that when a fluid (liquid or gas) is caused to travel through the chamber, the velocity of the fluid (liquid or gas) at various positions within said chamber is different and the fluid (liquid or gas) travels through the chamber according to a velocity profile. For example, the chamber may be rectangular in shape and may include, for example, a top wall, bottom wall and two side walls. The top wall and a bottom wall may be parallel to each other, or substantially parallel to each other, and the distance between the top wall and the bottom is referred to as chamber height. The distance between the inlet port and outlet is referred to as chamber length when the chamber comprises one inlet port and one outlet port. The two side walls may be parallel to each other, or substantially parallel to each other, and the distance between the two side walls of the chamber is referred to as chamber width. The two side walls may be parts of a gasket or a spacer between the top wall and bottom wall. The gasket or spacer may be cut in the middle to form a rectangular thin channel with taper ends. Alternatively, the gasket or spacer may be cut in the middle to form thin channels of other shapes such as ellipse, circle, or any other shape. In certain embodiments, the chamber may be constructed so that the top wall and bottom wall are of a much greater magnitude than the side walls (e.g., both chamber length and chamber width are substantially greater than the chamber height for a chamber with a rectangular shape), thereby creating a thin chamber. For such a thin chamber having a rectangular channel in the middle, when a carrier medium is caused to travel through the thin rectangular channel (or called "travel through the chamber"), the velocity of the carrier medium in the chamber may follow a parabolic or a near-parabolic profile. The velocity of the carrier medium at the top and bottom walls is zero, and with increasing the distances from the top wall or from the bottom wall, the velocity of the carrier medium increases to a maximum value at the middle position between the top and bottom walls. In other embodiments, the chamber may be constructed so that the top wall and bottom wall are of a much smaller magnitude than the side walls (e.g., both chamber length and chamber height are substantially greater than the chamber width for a chamber with a rectangular shape), again creating a thin chamber. In addition to the rectangular shape of the chamber, the chamber may be of circular construction, elliptical, triangular, hexadecagonal, or of other geometrical shapes. The chamber may be constructed having a top wall, a bottom wall, and a gasket or a spacer between the top and bottom wall. The gasket or spacer may be cut in the middle to form rectangular thin channel with taper ends. Alternatively, the gasket or spacer may be cut in the middle to form thin channels of other shapes such as ellipse, circle, or any other shape. In the case of a thin rectangular channel where the top and bottom walls on two different planes are parallel to each other, the velocity of the carrier medium in the medium may follow a parabolic or a near-parabolic velocity profile. The velocity of the carrier medium at the top and bottom walls is zero, and with the increasing distances from the top wall or from the bottom wall, the velocity of the carrier medium increases to a maximum value at the middle position between the top and bottom walls. Preferably, for a rectangular channel, the width of the channel is from about 1 mm to about 20 cm, and the height of the channel is from about 20 micron to about 10 mm, and the length of the channel is from about 1 cm to about 200 cm, preferably, from about 10 cm to about 50 cm. As such, the present invention is not intended to be limited to a particular geometric shape and the chamber may be constructed of many different materials, for example, glass, polymeric material, plastics, quartz, coated metal, or the like, provided that the chamber has such structural characteristics that when a carrier medium is caused to travel through the chamber, the velocity of the medium at different positions in the chamber is different.

The apparatus can comprise two, or more than two electrode elements. Each of the electrode elements can be individually connected to one of a plurality of electrical conductor buses electrically connected to the electrical signal generator. The electrode elements can be adapted substantially longitudinally or latitudinally along a portion of the chamber. The electrode elements can be adapted along the interior or exterior surface of the chamber. The electrode elements can be configured on a plane substantially parallel to traveling direction of the carrier medium caused to travel through said chamber. Preferably, the electrode elements configured in a plane form an electrode array. The electrode array may be an interdigitated electrode array, interdigitated castellated electrode array, interdigitated electrode array with arc-shape tip extensions. Preferably, the electrode element is a metal layer, e.g., a gold layer, coated on a surface of the chamber. Other metals such as platinum, aluminum, chromium, titanium, copper and silver may also be used.

The electrical signal generator for energizing the electrode element to create the dielectrophoretic force may be an AC signal source capable of varying magnitude and frequency of electrical signals.

The apparatus can comprise a single piezoelectric transducer or comprise a plurality of piezoelectric transducers. The plurality of piezoelectric transducers may be energized via common electrical signals or via different electrical signals. The plurality of piezoelectric transducers can be adapted along the interior or exterior surface of the chamber. The plurality of piezoelectric transducers can also be configured on a plane substantially parallel to traveling direction of the carrier medium that is caused to travel through the chamber.

Preferably, the electrical signal generator for energizing the piezoelectric transducer to create the acoustic force is capable of varying magnitude and frequency of said electrical signals.

Common electrical conductor buses may be used to connect a plurality of electrode elements to the signal generator. The common electrical conductor buses may be fabricated by the same process as the fabricated electrode elements in the apparatus, or may be one or more conducting assemblies, such as a ribbon conductor, metallized ribbon or metallized plastic. For an interdigitated electrode array, alternating electrode elements along the array may be connected together so as to receive electrical signals from the signal generator. The electrical generator may be a DC voltage supply capable of generating voltages of varying magnitude. Voltage signals desired for the apparatuses and methods of the present invention are in the range of about 0 to about 15 volts, and more preferably between about 0 to about 10 volts. The signal generator may be a signal generator capable of generating signals of varying voltage and frequency and may be, for example, a function generator, such as a Hewlett Packard generator Model No. 8116A. Signals desired for the apparatuses and methods of the present invention are in the range of about 0 to about 15 volts, and about 0.1 Hz to about 500 MHz, and more preferably between about 0 to about 10 volts, and about 0.1 kHz to 10 MHz. These frequencies are exemplary only, as the frequency required for matter discrimination using dielectrophoresis forces is dependent upon the conductivity of, for example, the cell suspension medium. Further, the desired frequency is dependent upon the characteristics of the matter to be discriminated. The discrimination obtained depends on the shape, size and configuration of the electrode elements, for example. In an exemplary embodiment, the signals are sinusoidal, however it is possible to use signals of any periodic or aperiodic waveform. The electrical signals may be developed in one or more electrical signal generators that are capable of varying voltage and frequency of electrical signals.

In a preferred embodiment, the chamber of the apparatus comprises a tube. The electrode element and/or the piezoelectric transducer, or a plurality thereof, can be adapted along the interior surface of the tube. Alternatively, the electrode element and/or the piezoelectric transducer, or a plurality thereof, can be adapted along the exterior surface of the tube.

In another preferred embodiment, the chamber comprises a top wall, a bottom wall, and two side walls. The electrode element and/or the piezoelectric transducer, or a plurality thereof, can be configured on the top wall of the chamber. Alternatively, the electrode element and/or the piezoelectric transducer, or a plurality thereof, can be configured on the bottom wall of the chamber. In another configuration, the electrode element and/or the piezoelectric transducer, or a plurality thereof, can be adapted on opposing surfaces of the chamber. Preferably, the chamber height between the top and bottom walls is about half wavelength of the standing acoustic wave.

In still another preferred embodiment, the apparatus consists essentially of, or consists of: a) a chamber having at least one inlet port and at least one outlet port, said chamber having such structural characteristics that when a carried medium is caused to travel through said chamber, the traveling velocity of said carried medium at various positions within said chamber is different; b) at least two electrode elements adapted along a portion of said chamber, wherein said electrode elements can be energized via at least one electrical signal provided by an electrical signal generator to create an electrical field, thereby causing at least one dielectrophoretic force having components normal to the traveling direction of said carrier medium on a matter in said carrier medium; and c) at least one piezoelectric transducer adapted along a portion of said chamber, wherein said piezoelectric transducer can be energized via at least one electrical signal provided by an electrical signal generator to create an acoustic wave, thereby causing at least one acoustic force having components normal to the traveling direction of said carrier medium on a matter in said carrier medium.

D. Methods of Discriminating a Matter using Acoustic Force, or Acoustic Force with Electrophoretic or Dielectrophoretic Force In still another aspect, the present invention provides a "continuous-mode" method of discriminating a matter using acoustic forces in field flow fractionation, which method comprises: a) obtaining an apparatus described in Section A; b) introducing a carrier medium containing a matter to be discriminated into the chamber of the apparatus via its inlet port, wherein said introducing causes the carrier medium to travel through the chamber according to a velocity profile; c) applying at least one electrical signal provided by an electrical signal generator to the piezoelectric transducer, wherein said energized piezoelectric transducer creates an acoustic wave, thereby causing at least one acoustic force on said matter having components normal to the traveling direction of said carrier medium travelling through said chamber; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. This is a continuous mode of acoustic-field-flow-fractionation (acoustic-FFF). It can be used with any apparatus described in Section A.

In still another aspect, the present invention provides a "batch-mode" method of discriminating a matter using acoustic forces in field flow fractionation, which method comprises: a) obtaining an apparatus described in Section A; b) loading a carrier medium into the chamber of apparatus via its inlet port until the chamber is filled with the carrier medium; c) delivering, e.g., injecting, a sample that contains a matter to be discriminated into the carrier medium in the chamber; d) applying at least one electrical signal provided by an electrical signal generator to the piezoelectric transducer, wherein said energized piezoelectric transducer creates an acoustic wave, thereby causing at least one acoustic force on said matter; e) introducing the carrier medium into the chamber of the apparatus via its inlet port, wherein said introducing causes the carrier medium to travel through the chamber according to a velocity profile; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. This "batch-mode" of acoustic-FFF can be used with any apparatus described in Section A.

In the above "batch-mode" method of acoustic-FFF, preferably, prior to the introducing of carrier medium into the chamber that causes the carrier medium to travel through the chamber according to a velocity profile (step e), applying electrical signal to the piezoelectric transducer to cause acoustic force on said matter results in the matter being displaced into an equilibrium position along a direction normal to the traveling direction of the carrier medium traveling through the chamber.

In still another aspect, the present invention provides a "continuous-mode" method of discriminating a matter using electrophoretic and acoustic forces in field flow fractionation, which method comprises: a) obtaining an apparatus described in above Section B; b) introducing a carrier medium containing a matter to be discriminated into the apparatus via its inlet port, wherein said introducing causes the carrier medium to travel through the chamber according to a velocity profile; c) applying at least one electrical signal provided by an electrical signal generator to the electrode elements, wherein said energized electrode elements creates an electrical field, thereby causing at least one electrophoretic force on said matter having components normal to the traveling direction of said carrier medium travelling through said chamber; and d) applying at least another electrical signal provided by an electrical signal generator to the piezoelectric transducer, wherein said energized piezoelectric transducer creates an acoustic wave, thereby causing at least one acoustic force on said matter having components normal to the traveling direction of said carrier medium travelling through said chamber; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. Any of the apparatuses described in Section B can be used in the present method of the continuous-mode of acoustic-electrophoretic-field-flow-fractionation (acoustic-E-FFF).

In yet another aspect, the present invention provides a "batch-mode" method of discriminating a matter using electrophoretic and acoustic forces in field flow fractionation, which method comprises: a) obtaining an apparatus described in above Section B; b) loading a carrier medium into the chamber of apparatus via its inlet port until the chamber is filled with the carrier medium; c) delivering, e.g., injecting, a sample that contains a matter to be discriminated into the carrier medium in the chamber; d) applying at least one electrical signal provided by an electrical signal generator to the electrode element, wherein said energized electrode element creates an electrical field, thereby causing at least one electrophoretic force on said matter; e) applying at least another electrical signal provided by an electrical signal generator to the piezoelectric transducer, wherein said energized piezoelectric transducer creates an acoustic wave, thereby causing at least one acoustic force on said matter; f) introducing the carrier medium into the chamber of the apparatus via its inlet port, wherein said introducing causes the carrier medium to travel through the chamber according to a velocity profile; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. Any of the apparatuses described in Section B can be used in the present method of the "batch-mode" of acoustic-E-FFF.

In the above described "batch-mode" of acoustic-E-FFF method, preferably, prior to the introducing of carrier medium into the chamber that causes the carrier medium to travel through the chamber according to a velocity profile (step f), applying electrical signal to the electrode element to cause electrophoretic force on said matter and applying electrical signal to the piezoelectric transducer to cause acoustic force on said matter result in the matter being displaced into an equilibrium position along a direction normal to the traveling direction of the carrier medium traveling through the chamber.

In yet another aspect, the present invention provides a "continuous-mode" method of discriminating a matter using dielectrophoretic and acoustic forces in field flow fractionation, which method comprises: a) obtaining an apparatus described in the above Section C; b) introducing a carrier medium containing a matter to be discriminated into the apparatus via its inlet port, wherein said introducing causes the carrier medium to travel through the chamber of the apparatus according to a velocity profile; c) applying at least one electrical signal provided by an electrical signal generator to the electrode element, wherein said energized electrode element creates a non-uniform electrical field, thereby causing at least one dielectrophoretic force on said matter having components normal to the traveling direction of said carrier medium travelling through said chamber; and d) applying at least another electrical signal provided by an electrical signal generator to the piezoelectric transducer, wherein said energized piezoelectric transducer creates an acoustic wave, thereby causing at least one acoustic force on said matter having components normal to the traveling direction of said carrier medium travelling through said chamber; whereby said matter is displaced to a position within said carrier medium along a direction normal to the traveling direction of the carrier medium traveling through the chamber and discriminated according to its position within said carrier medium along the direction normal to the traveling direction of the carrier medium traveling through the chamber. Any apparatus described in Section C can be used in the present method of the "continuous-mode" of acoustic-dielectrophoretic-field-flow-fractionation (acoustic-DEP-FFF).

In yet another aspect, the present invention provides a "batch-mode" method of discriminating a matter using dielectrophoretic and acoustic forces in field flow fractionation, which method comprises: a) obtaining an apparatus described in above Section C; b) loading a carrier medium into the chamber of apparatus via its inlet port until the chamber is filled with the carrier medium; c) delivering, e.g., injecting a sample that contains a matter to be discriminated into the carrier medium in the chamber; d) applying at least one electrical signal provided by an electrical signal generator to the electrode element, wherein said energized electrode element creates a non-uniform electrical field, thereby causing at least one dielectrophoretic force on said matter; e) applying at least another electrical signal provided by an electrical signal generator to the piezoelectric transducer, wherein said energized piezoelectric transducer creates an acoustic wave, thereby causing at least one acoustic force on said matter; f) introducing the carrier medium into the chamber of the apparatus via its inlet port, wherein said introducing causes the carrier medium to travel through the chamber according to a velocity profile; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. Any of the apparatuses described in Section C can be used in the present method of "batch-mode" of acoustic-DEP-FFF.

In the above described "batch-mode" of acoustic-DEP-FFF method, preferably, prior to the introducing of carrier medium into the chamber that causes the carrier medium to travel through the chamber according to a velocity profile (step f), applying electrical signal to the electrode element to cause dielectrophoretic force on said matter and applying electrical signal to the piezoelectric transducer to cause acoustic force on said matter result in the matter being displaced into an equilibrium position along a direction normal to the traveling direction of the carrier medium traveling through the chamber.

In the above acoustic-E-FFF or acoustic-DEP-FFF methods, identical, but preferably, different electric signals can be used to generate the acoustic force and the electrophoretic or the dielectrophoretic force.

In the above acoustic-E-FFF or acoustic-DEP-FFF method, the acoustic force and the electrophoretic or the dielectrophoretic force can be generated simultaneously or sequentially.

The above acoustic-FFF, acoustic-E-FFF and acoustic-DEP-FFF methods can further comprise a step of discriminating the matter according to the velocity profile of carrier medium travelling through the chamber and the matter moves within the chamber at velocities dependent on its displacement within the velocity profile.

The above acoustic-FFF, acoustic-E-FFF and acoustic-DEP-FFF methods can further comprise a step of displacing the discriminated matter from the apparatus, and preferably results in the separation of the discriminated matter from each other. After being displaced within the carrier medium travelling through the chamber of the present invention, the displaced matter may exit from the outlet port or ports at a time dependent on the displacement of the matter within the velocity profile of the carrier medium traveling through the chamber. Specifically, matter at different levels of displacement within the velocity profile travels at different speeds. Therefore, the displaced matter is discriminated by its displacement within the velocity profile and by its traveling speed. Matter that is displaced to different positions within the velocity profile travels at different velocities and exit from the outlet port or ports of the chamber at different times.

This velocity profile may be, for example, a hydrodynamic fluid profile such as a parabolic flow profile. For a chamber of rectangular shape, the chamber structural characteristics is defined by the chamber length, chamber width and chamber height. The velocity profile may be determined by knowing the flow rate of the fluid, and the chamber width, height and length. For example, for a rectangular chamber with the chamber length and width being substantially greater than the chamber height, a laminar flow may be established in the chamber. The velocity of the carrier medium at different positions is mainly determined by its distance from the chamber bottom walls, and the velocity profile is an approximately parabolic flow profile (or a near parabolic velocity profile), given by, $$V_m = 6\langle V_m \rangle \frac{z}{H}\left(1 - \frac{z}{H}\right),$$

where $\langle V_m \rangle$ is the average velocity of the carrier medium, H is the chamber height, $V_m$ is the velocity of the carrier medium located at a distance z from the chamber bottom wall. We would like to point out that the above parabolic velocity profile is only an approximation of the velocity profile under the condition that the chamber length and width in a rectangular chamber is much greater than the chamber height. That is why we use the term "near parabolic" profile or "near parabolic" profile for describing such velocity profile. Along the chamber width direction, the parabolic profile in the above equation is more accurate for the positions in the middle part across the chamber width than for the positions at the end regions. Similarly, along the chamber length direction, the parabolic profile in the above equation is more accurate for the positions in the middle part across the chamber length than for the positions at the end regions. The average velocity may be calculated according to the equation:

Average Velocity<$V_m$>=(flow rate)/(chamber width×chamber height (or thickness)).

Thus, the structural characteristics of the chamber that influence the velocity profile of the fluid flow in a rectangular chamber include: chamber width, chamber height (or chamber thickness) and chamber length. Chamber of different size and different geometrical shape will result in different velocity profile when a fluid is caused to travel through the chamber. Parameters that determine the velocity profile of the fluid flow include, but are not limited to, chamber geometrical dimensions; constrictions or expansions of the fluid flow path which may include, for example, those arising for a non-parallel disposition of opposing chamber walls, or from the presence of suitably-placed obstructions or vanes; surface roughness of the chamber walls; structural features of the chamber walls that give rise to periodic or aperiodic modifications of the thickness of the fluid stream, including the electrode elements and other surface structural configurations; and the geometrical form of the chamber which may be, for example, rectangular, circular, wedge-shaped, stepped, or the like.

In the above methods, the displaced matter may exit from one of a plurality of the outlet ports of the chamber dependent on its displacement within the velocity profile. In a preferred embodiment, the gravitational force acting on the matter acts in a direction normal to the traveling direction of the carrier medium in the chamber.

The present acoustic-FFF, acoustic-E-FFF and acoustic-DEP-FFF methods can be used to discriminate any matters. In specific embodiments, matters to be discriminated are cells, cellular organelles, viruses, molecules or an aggregate or complex thereof. Non-limiting examples of discriminatable cells include animal, plant, fungus, bacterium cultured or recombinant cells. Non-limiting examples of discriminatable cellular organelles include nucleus, mitochondria, chloroplasts, ribosomes, ERs, Golgi apparatuses, lysosomes, proteasomes, secretory vesicles, vacuoles or microsomes. Discriminatable molecules can be inorganic molecules such as ions, organic molecules or a complex thereof. Non-limiting examples of discriminatable ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of discriminatable organic molecules include amino acids, peptides, proteins, nucleosides, nucleotides, oligonucleotides, nucleic acids, vitamins, monosaccharides, oligosaccharides, carbohydrates, lipids or a complex thereof. The matters to be discriminated can be of any size. Preferably, the dimension of the matter to be discriminated is from about 0.01 micron to about 1000 micron.

MODES OF CARRYING OUT THE INVENTION

A. Definitions

Figure 1:
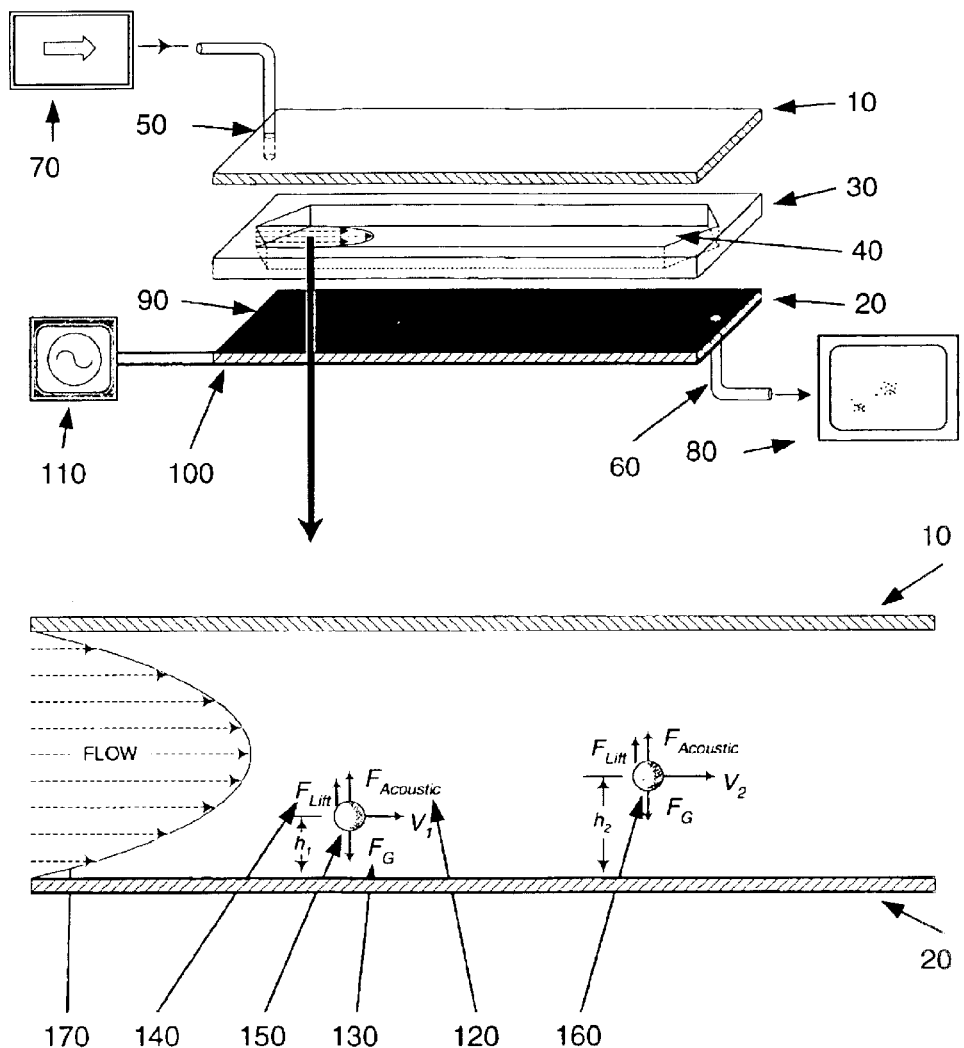
FIG. 1. Schematic diagram of an acoustic-FFF chamber with a rectangular channel cut in the middle. Also shown is the operation principle of the acoustic-FFF.

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein in any section of this application are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "matter" refers to particulate matter, solubilized matter, or any combination thereof.

As used herein, "electrode element (or electrode)" refers to a structure of highly electrically-conductive material over which an applied electrical voltage is constant or nearly-constant. Nearly-constant means that the voltage drop across such electrically-conductive structure is so small that sufficiently strong electrical field at the regions around the electrode elements can be produced when the electrical signals are applied to the electrode elements. Typically, the highly electrically-conductive materials include metal films (e.g., gold, platinum, titanium, chromium, etc) and semiconductor materials such as silicon doped with impurities (e.g., silicon doped with phosphorus, or arsenic, or antimony, or aluminum, or gallium, or indium), and other materials whose electrical conductivity is high. For this invention, highly electrically-conductive material refers to the material whose electrical conductivity is substantially larger than that of carrier medium used for the fractionation (e.g., the conductivity of the conductive material is twice or more than twice of that of the carrier medium). It is to be understood that these terms include all of the electrode configurations described in the present specification and claims.

As used herein, "electrode array" refers to a collection of more than one electrode elements. In an electrode array, each individual element may be displaced in a well-defined geometrical relationship with respect to one another. This array may be, for example, an interdigitated electrode array, an interdigitated castellated array, a polynomial array, an interdigitated electrode array having periodic triangular-shaped tips on the electrode elements (or arc-like tips, or rectangular tips), or the like. "Electrode array" may also include multiple electrode elements that have same or different geometrical shapes.

As used herein, "normal to the traveling direction" of the carrier medium travelling through the chamber refers to a direction which is substantially non-opposing and substantially nonlinear to the flow direction of the carrier medium traveling through the chamber. For example, when a carrier medium is caused to flow along the chamber length direction of a rectangular chamber, the "normal to the traveling direction" may be a direction across the chamber width, or across chamber height, or any direction in a plane parallel to the plane defined by the chamber width and chamber height, or any other direction that is non-opposing to the flow direction of the carrier medium. Ordinarily, the angle between the travelling direction and the "normal to the traveling direction" is from about 45 degree to about 135 degree. Preferably, the angle between the travelling direction and the "normal to the traveling direction" is from about 80 degree to about 100 degree. More preferably, the angle between the travelling direction and the "normal to the traveling direction" is from about 85 degree to about 95 degree.

As used herein, "fraction collectors (or collection wells or collection devices)" refers to storage and collection devices for discretely retaining the separated and/or discriminated and/or displaced matter.

As used herein, "characterization device" refers to any device that is capable of characterizing the separated and/or displaced and/or discriminated matter. Characterization device may be a particle counter that counts the particles and record the particle number and arrival time as they exit the chamber. Characterization device could be an assay device that is capable of performing further assay or analysis on separated matter.

As used herein, "piezoelectric transducer" refers a structure of "piezoelectric material" that can produce an electrical field when exposed to a change in dimension caused by an imposed mechanical force, and that can be energized by an applied electrical signal to produce mechanical stress in the materials. In the present invention, we apply AC electrical signals to the piezoelectric transducer and produce alternating mechanical stress in the material, that is coupled as an acoustic wave into the carrier medium used for fractionation and discrimination of matter.

As used herein, "structural characteristics of the chamber" refers to the structural properties of the chamber, including, but not limited to, the chamber geometrical shape, chamber dimensions, structure and composition of each of chamber components (e.g., top wall, bottom wall, side walls).

As used herein, "the traveling velocity of said carried medium at various positions within said chamber is different" means that the structural characteristics of the chamber is designed or chosen so that the traveling velocities of said carried medium at least two positions within said chamber are different. It is not necessary that the traveling velocities of said carried medium at all positions within said chamber are different. In many cases, it is sufficient that the traveling velocities of the carried medium at a certain height (or width), or within a certain plane normal to the travelling direction, is identical, but is different from the traveling velocities of the carried medium at another height (or width), or within another plane normal to the travelling direction.

As used herein, "matter is displaced to a position along a direction" means that the matter is caused to move to a position along a direction of interest under the influence of forces exerting on matter. Here the positions are identified as locations or points along the direction. For example, in a rectangular chamber comprising a top wall and a bottom wall that are separated by a thin gasket that is cut in the middle to form a thin, rectangular channel, a carrier medium containing the matter to be discriminated is caused to move along the channel length direction. Electrode elements and piezoelectric transducers are adapted on the chamber top and/or bottom walls. When electrical signals are applied to the electrode elements and piezoelectric transducers, acoustic forces and dielectrophoretic forces are produced on the matter that is placed in the carrier medium. These forces have components along the vertical direction, which are normal to the traveling direction of the chamber. These force components will cause the matter to move to various positions along the vertical direction. For example, the matter may be initially located close to the chamber bottom wall and may be caused to move to certain heights from the chamber bottom wall when the electrical signals are applied to energize electrode elements and piezoelectric transducers. In the present invention, the forces that influence the positions of "matter" include acoustic forces, electrophoretic forces, dielectrophoretic forces, gravitational forces, hydrodynamic lifting forces, thermal diffusion forces. For the matter whose positions are influenced by the thermal diffusion effects, the positions of "matter" along a direction refer to a distribution profile or a concentration profile of the matter along the direction. For the matter whose positions are not influenced by the thermal diffusion effects, the positions of "matter" along a direction refer to the locations of "matter" along the direction.

As used herein, "displacement within the velocity profile" refers to the displacement of matter within the velocity profile of the carrier medium traveling through the chamber. Here the displacement of the matter is identified within the frame of the velocity profile. The matter displaced to the fast-moving part of the velocity profile may be caused to move faster than the matter displaced to the slow-moving part of the velocity profile. For the matter whose positions are influenced by the thermal diffusion of the matter, the displacement of "matter" within the velocity profile refers to a re-distribution profile of the matter within the reference frame of the velocity profile. For the matter whose positions are not influenced by the thermal diffusion of the matter, the displacement of "matter" within the velocity profile refers to the displacement of "matter" within the reference frame of the velocity profile.

As used herein, "the matter being displaced into an equilibrium position along a direction" refers to the matter being caused to move to an equilibrium position along a direction of interest under the influence of forces exerting on matter. Here the equilibrium positions are identified as locations or points along the direction. The equilibrium positions refer to the positions at which the net force on the matter is zero, or almost zero so that the matter will remain on such equilibrium positions. For the matter whose positions are influenced by the thermal diffusion of the matter, the equilibrium position of "matter" along a direction refers to an equilibrium distribution profile of the matter along the direction. For the matter whose positions are not influenced by the thermal diffusion of the matter, the equilibrium position of "matter" along a direction refers to the location of "matter" along the direction when the matter is at force equilibrium.

As used herein, "the chamber's length is substantially greater than its width or height" means that, regardless of the actual chamber shape, the characteristic length of the chamber is at least twice as long as the characteristic width or height of the chamber. Preferably, the characteristic length of the chamber is at least three-times as long as the characteristic width or height of the chamber. More preferably, the characteristic length of the chamber is at least five-times as long as the characteristic width or height of the chamber. Although the width and height of the chamber can be identical or roughly identical, it is preferable that one it substantially longer than the other, e.g., the width being substantially longer than the height, or vice versa. For example, the characteristic width of the chamber can be at least twice, three-times or five-times, as long as the characteristic height, or vice versa.

For clarity of disclosure, and not by way of limitation, the detailed description of the invention is divided into the subsections that follow.

B. Exemplary Apparatuses

B.1. Acoustic-FFF Chamber.

FIG. 1 shows an embodiment of acoustic-FFF chamber and the operational principle of acoustic-FFF. The chamber has a top wall 10 and a bottom wall 20. The top wall and bottom wall are separated by a gasket or spacer 30 that has a rectangular channel 40 cut in it. The channel 40 has tapered ends. For clarity, the top wall 10, the gasket 30 and the bottom wall 20 are shown separated from each other. In use, these components are bound to each other to form an acoustic-FFF chamber. An inlet port 50 and an outlet port 60 are located on the top wall and bottom wall, at the inlet end and outlet end of the chamber, respectively. The inlet port 50 is connected with an infusion device 70 that can introduce carrier medium and introduce the matter to be discriminated into the chamber. The infusion device may be a syringe pump coupled with an injection valve (Wang et al., 1998; Huang et al., 1999; Yang et al., 1999). The outlet port 60 is connected with a collection or characterization device 80 that is capable of characterizing the matter that has been separated and discriminated after the acoustic-FFF process. The collection or characterization device may be a particle counter, a flow cytometer or a fractionation collector.

In the exemplary figure, the whole bottom wall 20 is a piezoelectric transducer. The top surface 90 and bottom surface 100 of the bottom wall 20 has been coated with metal films or other electrically conductive material. AC electrical signals from a signal generator 110 can be applied to the top surface 90 and bottom surface 100 of the piezoelectric transducer 20 to energize the piezoelectric transducer to produce an acoustic wave in the chamber in the direction normal to surfaces 90 and 100. The acoustic wave transmitted from the piezoelectric transducer is reflected back by the top wall 10. The superimposition of the transmitted wave from the piezoelectric transducer and the reflected wave from the top wall form the total acoustic wave field in the chamber. The total acoustic wave field may have two components, i.e., standing-wave component and traveling wave component. The ratio of the magnitude of the standing-wave component to the magnitude of the traveling-wave component is determined by the chamber height (i.e., the distance between the top wall and bottom wall), the wavelength of the acoustic wave, the acoustic properties of the top wall 10 and the bottom wall 20, the decaying factor for the acoustic wave in the carrier medium. In one embodiment, the chamber height is half wavelength of the standing acoustic wave, and a standing acoustic wave is established in the chamber. An acoustic pressure node exists at the center plane of the chamber. In another embodiment, the chamber height is larger or smaller than half wavelength of the standing acoustic wave.

In the example of FIG. 1, the bottom wall 20 of the chamber corresponds to a piezoelectric transducer. There may be many variations in adapting one or more piezoelectric transducers along the portions of the chamber. The piezoelectric transducers may be adapted on the top and/or the bottom walls. For adapting the piezoelectric transducer on the bottom wall, the transducer may be bound to a solid plate from the bottom side so that the solid plate forms the bottom surface of the chamber. The acoustic wave may be generated from the piezoelectric transducer and be coupled into the carrier medium placed in the chamber through the solid plate. Similarly, for adapting the piezoelectric transducer on the top wall, the transducer may be bound to a solid plate from the top side so that the solid plate forms the top surface of the chamber. The acoustic wave may be generated from the piezoelectric transducer and be coupled into the carrier medium placed in the chamber through the solid plate. The acoustic-FFF chamber shown in FIG. 1 comprises one piezoelectric transducer in the chamber. Multiple piezoelectric transducers may be employed in one chamber. These transducers may be adapted on the top wall in series, or on bottom wall in series, or on both top and bottom walls to form a piezoelectric transducer array. The multiple piezoelectric transducers may be energized by same or different electrical signals to produce acoustic waves in the chamber.

The matter being introduced into the chamber will experience different forces in the chamber. We consider the case that the matter introduced is microscopic particles and the chamber is disposed horizontally. These forces are:

Acoustic radiation force $F_{acoustic}$ 120 in the vertical direction pointing towards or away from the top (or bottom) wall, depending on a factor which relates to the densities of the particles and the suspending medium, and to the acoustic impedance of the of the particles and the medium. The force $F_{acoustic}$ 120 may be a component of total acoustic force acting on the particle.

Gravitational force $F_G$ 130 levitating or sedimenting the particles, depending on the relative magnitude of the densities of the particles and the suspending medium.

Hydrodynamic lifting force $F_{lift}$ 140 that tends to drive the particles away from the chamber walls. Various theoretical and experimental studies have been conducted on such hydrodynamic forces yet its nature remains in question (Williams et al., 1992; 1994; 1996; 1997). However, it is generally accepted that this force plays an important role only when the particles are very close to the chamber walls (e.g., <5 micrometer in a chamber of 200 micrometer thick). Some recent work in DEP-FFF (Huang et al., 1997; Wang et al., 1998) shows that this force plays little role in DEP-FFF operation.

These three forces are acted on the particles, driving the particles towards equilibrium positions at which these forces balance so that the net force acting on individual particles in the vertical direction is zero, i.e., $$F_{acoustic}(z)+F_{lift}(z)-F_G=0$$

Particles of different properties (e.g., size, geometrical shape, density, acoustic impedance) equilibrate to different height positions. For example, particles 150 and 160 are displaced to different heights from the chamber bottom wall. When a fluid flow is introduced by infusing the carrier medium through inlet port 50 into the chamber, a flow velocity profile 170 is generated. The traveling direction in this case is parallel to the chamber top and bottom walls, and points from the chamber inlet end towards the chamber outlet end. The carrier medium at various positions of the chamber exhibit different velocities. For the example shown in FIG. 1, when the chamber length (i.e., the length of the channel cut in the middle) and chamber width (i.e., the width of the channel) is substantially greater than the chamber height (i.e., the distance between the top wall and bottom wall), the velocity of the carrier medium at the positions not close to the channel walls defined by the gasket follows an approximate parabolic velocity profile in the vertical direction, $$V_m = 6\langle V_m\rangle \frac{z}{H}\left(1 - \frac{z}{H}\right)$$

where $V_m$ is the velocity of the medium at a height z from the chamber bottom wall, $\langle V_x\rangle$ is the average velocity of the medium, H is the chamber height. Thus, a near-parabolic velocity profile is established along the vertical direction for the carrier medium in such a chamber. Thus, particles 150 and 160 may be discriminated according to the height positions $h_1$ and $h_2$ along a vertical direction that is normal to the traveling direction of the carrier medium. Furthermore, because of the velocity profile, the particles 150 and 160 may be further discriminated according to the vertical positions within the velocity profile. Even furthermore, the particles 150 and 160 are caused to travel across the chamber at different velocities V, and $V_2$. If the particles 150 and 160 are introduced into the chamber at similar time, the particles 150 and 160 will exit the chamber at different times because they are transported through the chamber at different velocities. The particles of different properties (e.g.: size, density, geometry, acoustic impedance) may be displaced to different positions along the vertical direction, may be discriminated according to their displacement positions along the vertical direction or within the velocity profile, maybe discriminated according to the velocities at which the particles travel through the chamber or according to the exit times of the particles leaving the chamber. Particles of different properties may be fractionated into sub-populations. Alternatively, particles displaced to different heights may be fractionated into sub-populations as they exit the chamber through different outlet ports if the different outlet ports are arranged vertically along the outlet end of the chamber.

In the above discussion, the chamber has been considered as being disposed horizontally. However, the chamber may be disposed along any direction or having any angle with respect to the horizontal plane. In these cases, we would still consider forces acting on the matter to be discriminated primarily along the direction normal to the traveling direction of the carrier medium. The difference between these cases and the above case where the chamber is disposed horizontally is that the gravitational force may be different. In the above case, the gravitational force acts in a direction perpendicular to the traveling direction of the carrier medium. In the cases where the chamber is not disposed horizontally, the gravitational force may act in a direction not perpendicular to the traveling direction of the carrier medium. Thus, only a component of the gravitational force should be considered for analyzing the forces exerting on the matter to be discriminated along a direction perpendicular to the traveling direction of the carrier medium.

The velocity profile in the rectangular chamber shown in FIG. 1 depends on the structural characteristics of the chamber. When the chamber length and width is substantially larger than the chamber height, a parabolic or a near-parabolic velocity profile along the vertical direction exits in the chamber. The reason for being "near-parabolic" is that the velocity profile at the positions close to the gasket walls does not follow the "parabolic profile". When the chamber width and the chamber height are of similar sizes, the velocity of the carrier medium in the chamber will follow other velocity profile than the "parabolic velocity profile" discussed above. Furthermore, the top and the bottom walls have been considered as flat and parallel to each other during the above discussions. When the top wall and/or the bottom wall are not flat, or when the top wall and the bottom wall are not parallel to each other, or when the top wall or the bottom wall is modified with structures elements of various thickness, the velocity profile of the carrier medium will be different from the "near-parabolic velocity profile" described above.

Figure 2:
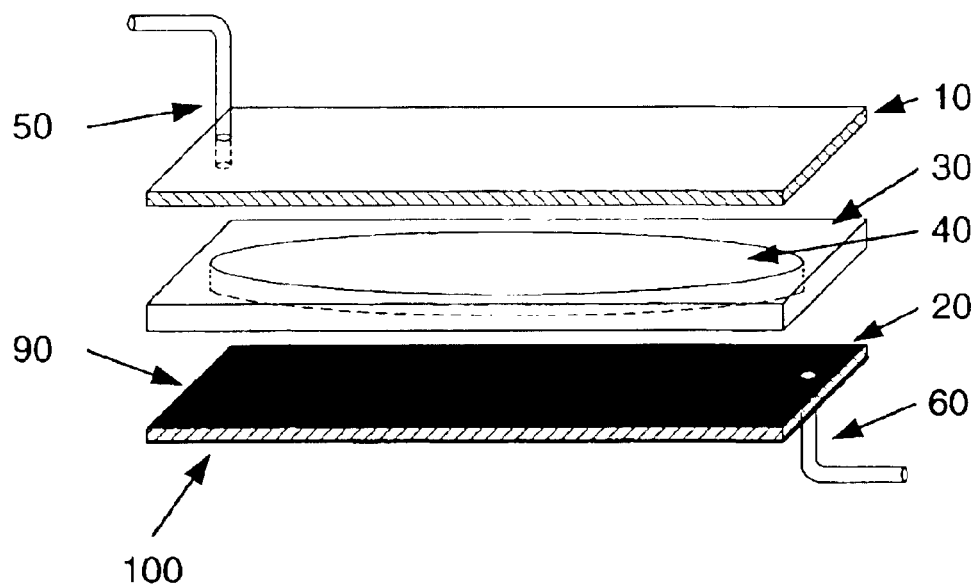
FIG. 2. Schematic diagram of an acoustic-FFF chamber with an ellipse-shaped channel cut in the middle.
Figure 3:
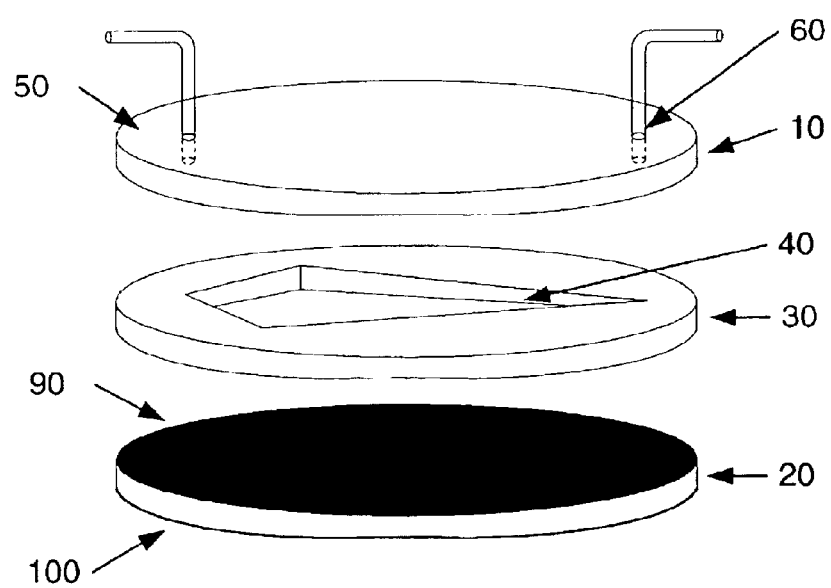
FIG. 3. Schematic diagram of an ellipse-shaped acoustic-FFF chamber with a channel cut in the middle.

To produce different velocity profile of the carrier medium, the gasket 30 between the top wall 10 and the bottom wall 20 may be cut in the middle to form channels of other shapes. For example, the channel 40 in the acoustic-FFF chamber shown in FIG. 2 has an ellipse shape. When a carrier medium is caused to travel through such a chamber, the velocity profile of the carrier medium will be different from that for the chamber shown in FIG. 1. Similarly, the channel for the chamber shown in FIG. 3 will result in a unique velocity profile for the carrier medium when it is caused to travel through the channel.

The above discussion of the acoustic-FFF chamber has focused on the discrimination of particles where we ignored the influence of thermal diffusion effects. For matter of small sizes to be discriminated in an acoustic-FFF chamber, it may be necessary to take into account the thermal diffusion forces. In such cases, the position of the matter being displaced along a direction or within a velocity profile by the applied forces refers to the distribution of the matter that has been influenced by the applied forces. Such distributions of the matter along a direction or within a velocity profile refer to the concentration profile or the distribution profile of the matter along the direction or within the velocity profile.

Figure 4:
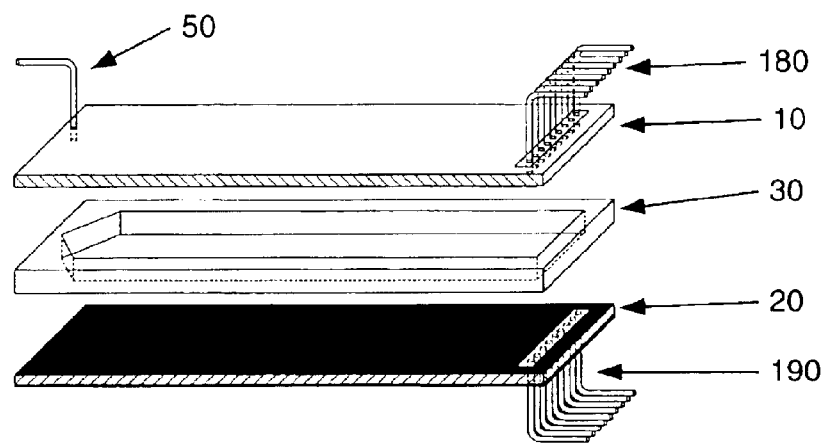
FIG. 4. Schematic diagram of an acoustic-FFF chamber with multiple outlet ports at the outlet end of the chamber.

The acoustic-FFF chamber may have one or more inlet ports through which the matter to be discriminated and the carrier medium are introduced. The chamber may have one or more outlet ports through which the discriminated matter and the carrier medium may exit the chamber. The inlet and outlet ports may be located on the top or/and bottom walls of the chamber. The inlet and outlet ports may be holes (as small as from about several microns or as large as about several mm in diameter) drilled on the chamber top and/or bottom walls. PEEK or plastic, or metal tubing may be inserted into the holes and serve as the fluid connection between the chamber and the external fluid-circuits such as infusion devices or collection devices. Alternatively, the inlet and outlet port may be a slot (from about micron(s) to about mm in width) drilled across the chamber outlet end. Multiple tubing, arranged in a ribbon form, can be interfaced with such slots. In the exemplary chamber shown in FIG. 4, a single inlet port—a hole—is located at the bottom wall of the chamber. The two outlet ports 180 and 190, positioned at both the top and the bottom walls, are the thin slots cut at the walls. A plurality of tubing arranged in a ribbon form is used to connect to the thin slots as the outletports. The two outlet ports arranged at the bottom and top walls correspond to the split-configuration employed in many field-flow-fractionation devices (Springston et al, 1987; Lee et al, 1989; Levin and Giddings, 1991).

B.2. Acoustic-Electrical-FFF Chamber.

Figure 5:
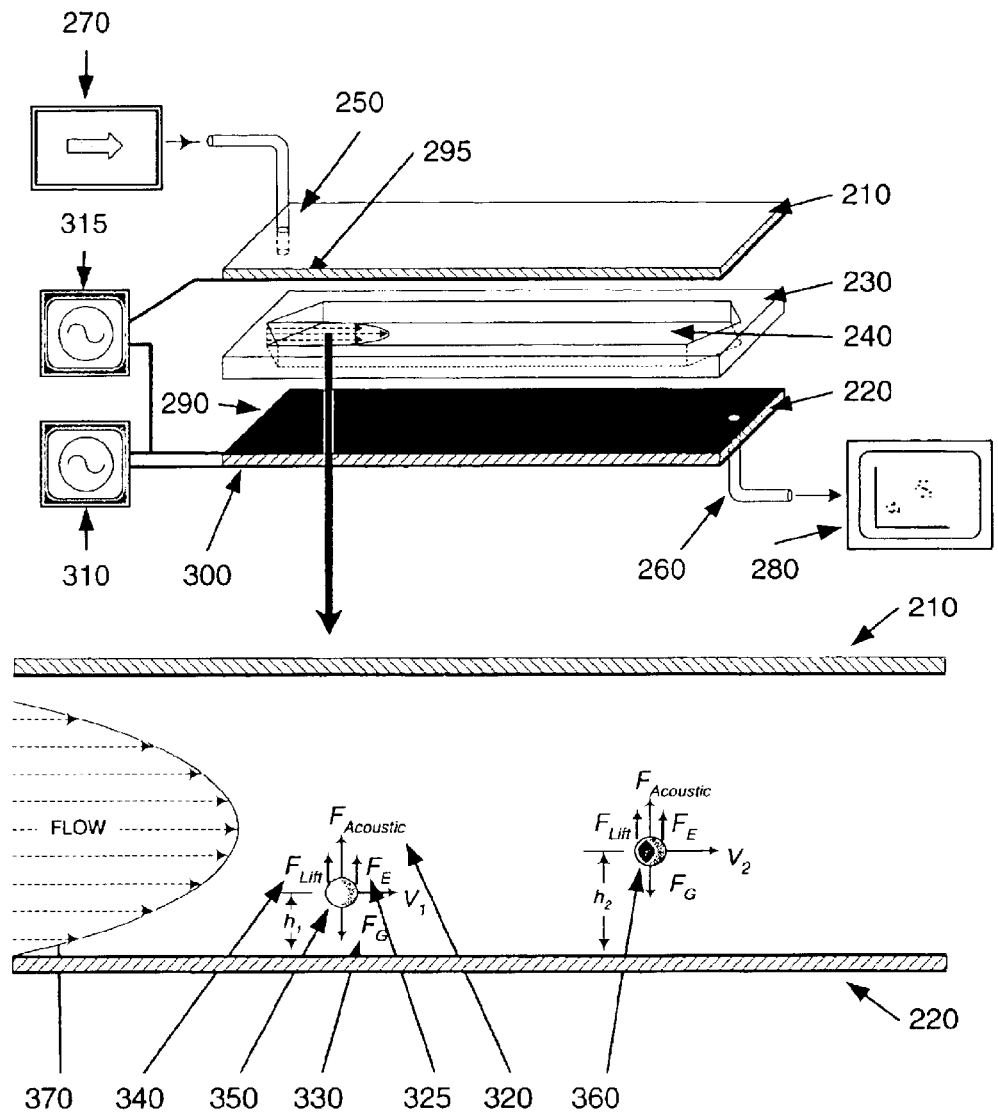
FIG. 5. Schematic diagram of an acoustic-E-FFF chamber with a rectangular channel cut in the middle. Also shown is the operation principle of the acoustic-E-FFF.

FIG. 5 shows an embodiment of acoustic-E-FFF chamber and the operational principle of acoustic-E-FFF. The chamber has a top wall 210 and a bottom wall 220. The top wall and bottom wall are separated by a gasket or spacer 230 that has a rectangular channel 240 cut in it. The channel 240 has tapered ends. For clarity, the top wall 210, the gasket 230 and the bottom wall 220 are shown separated from each other. In use, these components are bound to each other to form an acoustic-E-FFF chamber. An inlet port 250 and an outlet port 260 are located on the top wall and bottom wall, at the inlet end and outlet end of the chamber, respectively. The inlet port 250 is connected with an infusion device 270 that can introduce carrier medium and introduce the matter to be discriminated into the chamber. The infusion device may be a syringe pump coupled with an injection valve (Wang et al., 1998; Huang et al., 1999; Yang et al., 1999). The outlet port 260 is connected with a collection or characterization device 280 that is capable of characterizing the matter that has been separated and discriminated after the acoustic-E-FFF process. The collection or characterization device may be a particle counter, a flow cytometer or a fractionation collector.

In the exemplary FIG. 5, the whole bottom wall 220 is a piezoelectric transducer. The top surface 290 and bottom surface 300 of the bottom wall 220 has been coated with metal films or other electrically conductive material. AC electrical signals from a signal generator 310 can be applied to the top surface 290 and bottom surface 300 of the piezoelectric transducer 220 to energize the piezoelectric transducer to produce an acoustic wave in the chamber in the direction that is normal to the surfaces 290 and 300. The acoustic wave transmitted from the piezoelectric transducer is reflected back by the top wall 210. The superimposition of the transmitted wave from the piezoelectric transducer and the reflected wave from the top wall form the total acoustic wave field in the chamber. The total acoustic wave field may have two components, i.e., standing-wave component and traveling wave component. The ratio of the magnitude of the standing-wave component to the magnitude of the traveling-wave component is determined by the chamber height (i.e., the distance between the top wall and bottom wall), the wavelength of the acoustic wave, the acoustic properties of the top wall 210 and the bottom wall 220, the decaying factor for the acoustic wave in the carrier medium. In one embodiment, the chamber height is half wavelength of the standing acoustic wave, and a standing acoustic wave is established in the chamber. An acoustic pressure node exists at the center plane of the chamber. In another embodiment, the chamber height is larger or smaller than half wavelength of the standing acoustic wave.

In the example of FIG. 5, the bottom wall 220 of the chamber corresponds to a piezoelectric transducer. There may be many variations in adapting one or more piezoelectric transducers along the portions of the chamber. The piezoelectric transducers may be adapted on the top and/or the bottom walls. For adapting the piezoelectric transducer on the bottom wall, the transducer may be bound to a solid plate from the bottom side so that the solid plate forms the bottom surface of the chamber. The acoustic wave may be generated from the piezoelectric transducer and be coupled into the carrier medium placed in the chamber through the solid plate. Similarly, for adapting the piezoelectric transducer on the top wall, the transducer may be bound to a solid plate from the top side so that the solid plate forms the top surface of the chamber. The acoustic wave may be generated from the piezoelectric transducer and be coupled into the carrier medium placed in the chamber through the solid plate. The acoustic-E-FFF chamber shown in FIG. 5 comprises one piezoelectric transducer in the chamber. Multiple piezoelectric transducers may be employed in one chamber. These transducers may be adapted on the top wall in series, or on bottom wall in series, or on both top and bottom walls to form a piezoelectric transducer array. The multiple piezoelectric transducers may be energized by same or different electrical signals to produce acoustic waves in the chamber.

In the exemplary FIG. 5, electrode elements employed for generating an electric field in the chamber correspond to the top surface 290 of the bottom wall 220, and the bottom surface 295 of the top wall 210. The top surface 290 of the bottom wall 220 and the bottom surface 295 of the top wall 210 have been coated with metal films or other electrically conductive material. Thus, DC electrical signals or low-frequency-AC signals from a signal generator 315 may be applied across the surface 290 and 295 to produce an electric field that in the direction normal to the top wall and the bottom wall. The matter being introduced into such an electric field will experience electrophoretic forces that depend on the field strength and the effective charge of the matter.

Figure 6:
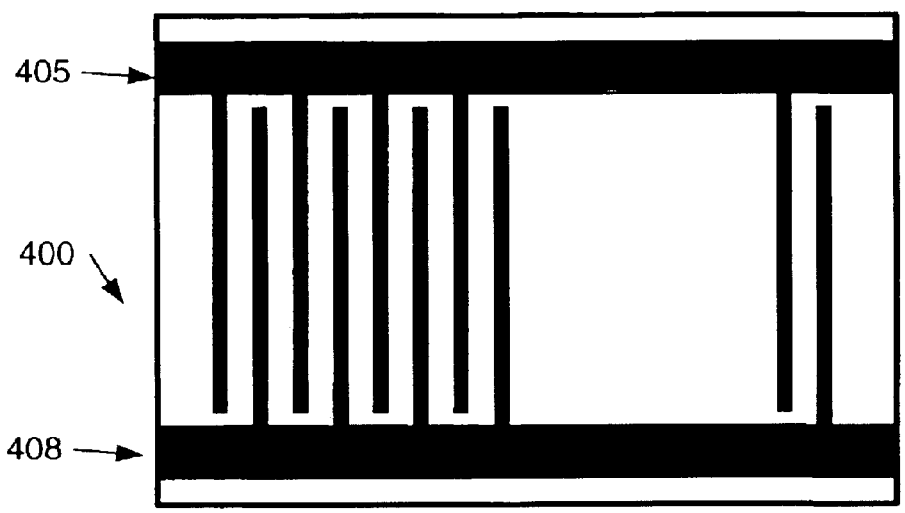
FIG. 6. Schematic diagrams for electrode arrays that may be used for acoustic-E-FFF apparatus. (A) The interdigitated electrode array. (B) The interdigitated castellated electrode array.
Figure 6:
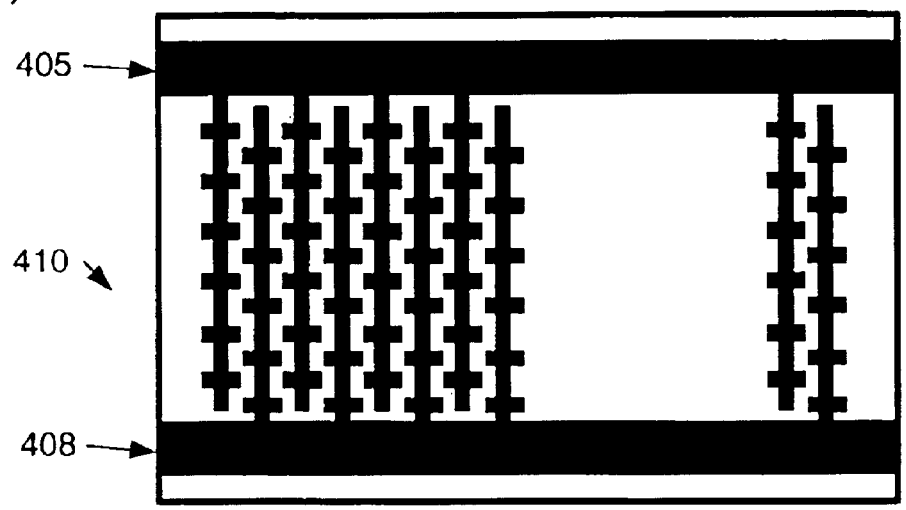

In the example shown in FIG. 5, the top surface 290 of the bottom wall 220 is used as one electrode element for generating electric field and also used as one electrode for energizing the piezoelectric transducer. In general, the electrode elements for generating the electrical field and for energizing the piezoelectric transducer may be different. Furthermore, the electrode elements for generating the electric field may be covering only portions of the bottom surface of the top wall, or the portions of the top surface of the bottom wall. Electrode arrays of different configurations may be utilized on these surfaces (i.e., the bottom surface of the top wall or the top surface of the bottom wall). FIG. 6 shows an interdigitated electrode array 400 and an interdigitated castellated electrode array 410. The electrode elements may be adapted substantially latitudinally (as shown in FIG. 6A or FIG. 6B) or longitudinally (i.e., the electrode elements in FIG. 6A are turned by 90 degree) along a portion of the chamber. Individual electrode elements in these electrode arrays are connected to one of two common electrical conductor buses 405 and 408. Electrode elements are energized to produce electric fields when electrical signals from signal sources are connected to such electrical conductor buses. For these cases where electrode arrays are used to produce electric fields, various electrical signal connection modes for producing electrical field and for energizing the piezoelectric transducers may be utilized. For example, the bottom surface of the top wall forms a conductive plane as one electrode element used to produce electrical field in the chamber, the bottom wall forms a piezoelectric transducer whose bottom surface is covered with conductive thin film and top surface is covered with an interdigitated electrode array such as that shown in FIG. 6A. The signal for producing electrical field in the chamber may be applied across the bottom surface of the top wall and either one or both electrical conductor buses (405 and 408 in FIG. 6A) in the interdigitated array. The signal for producing acoustic waves in the chamber may be applied across the bottom surface of the bottom wall and either one or both electrode buses (405 and 408 in FIG. 6A) in the interdigitated array.

The matter being introduced into an acoustic-E-FFF chamber will experience different forces in the chamber. We consider the case that the matter introduced is microscopic particles and the chamber is disposed horizontally. Referring to FIG. 5, these forces are:

Acoustic radiation force $F_{acoustic}$ 320 in the vertical direction pointing towards or away from the top (or bottom) wall, depending on a factor which relates to the densities of the particles and the suspending medium, and to the acoustic impedance of the of the particles and the medium. The acoustic force $F_{acoustic}$ 320 may be a component of the total acoustic radiation force acting on particles.

Electrophoretic force $F_E$ 325 in the vertical direction on the charged particles. Depending on whether the particles are positively or negatively charged and depending on the direction of the DC electrical field, this force points towards or away from the chamber bottom wall. The electrophoretic force $F_E$ 325 may be a component of the total electrophoretic force acting on particles.

Gravitational force $F_G$ 330 levitating or sedimenting the particles, depending on the relative magnitude of the densities of the particles and the suspending medium.

Hydrodynamic lifting force $F_{lift}$ 340 that tends to drive the particles away from the chamber walls. Various theoretical and experimental studies have been conducted on such hydrodynamic forces yet its nature remains in question (Williams et al., 1992; 1994; 1996; 1997). However, it is generally accepted that this force plays an important role only when the particles are very close to the chamber walls (e.g.: <5 micrometer in a chamber of 200 micrometer thick). Some recent work in DEP-FFF (Huang et al., 1997; Wang et al., 1998) shows that this force plays little role in DEP-FFF operation.

These forces are acted on the particles, driving the particles towards equilibrium positions at which these forces balance so that the net force acting on individual particles in the vertical direction is zero, i.e., $$F_{acoustic}(z) + F_{lift}(z) + F_E(z) - F_G = 0$$

Particles of different properties (e.g.: size, geometrical shape, density, charge, acoustic impedance) equilibrate to different height positions. For example, particles 350 and 360 are displaced to different heights $h_1$ and $h_2$ from the chamber bottom wall. When a fluid flow is introduced by infusing the carrier medium through inlet port 250 into the chamber, a flow velocity profile 370 is generated. The traveling direction in this case is parallel to the chamber top and bottom walls, and points from the chamber inlet end towards the chamber outlet end. The carrier medium at various positions of the chamber exhibit different velocities. For the example shown in FIG. 5, when the chamber length (i.e., the length of the channel cut in the middle) and chamber width (i.e., the width of the channel) is substantially greater than the chamber height (i.e., the distance between the top wall and bottom wall), the velocity of the carrier medium at the positions not close to the channel walls defined by the gasket follows an approximate parabolic velocity profile in the vertical direction, $$V_m = 6 \langle V_m \rangle \frac{z}{H} \left(1 - \frac{z}{H}\right)$$

where $V_m$ is the velocity of the medium at a height z from the chamber bottom wall, $\langle V_m \rangle$ is the average velocity of the medium, H is the chamber height. Thus, a near-parabolic velocity profile is established along the vertical direction for the carrier medium in such a chamber. Thus, particles 350 and 360 may be discriminated according to the height positions ($h_1$ versus $h_2$) along a vertical direction that is normal to the traveling direction of the carrier medium. Furthermore, because of the velocity profile, the particles 350 and 360 may be further discriminated according to the vertical positions within the velocity profile. Even furthermore, the particles 350 and 360 are caused to travel across the chamber at different velocities V, and $V_2$. If the particles 350 and 360 are introduced into the chamber at similar time, the particles 350 and 360 will exit the chamber at different times because they are transported through the chamber at different velocities. The particles of different properties (e.g.: size, density, geometry, charge, acoustic impedance) may be displaced to different positions along the vertical direction ($h_1$ versus $h_2$); may be discriminated according to their displacement positions along the vertical direction or within the velocity profile; maybe discriminated according to the velocities at which the particles travel through the chamber ($V_1$ versus $V_2$) or according to the exit times of the particles leaving the chamber. Particles of different properties may be fractionated into subpopulations. Alternatively, particles displaced to different heights may be fractionated into sub-populations as they exit the chamber through different outlet ports if the different outlet ports are arranged vertically along the outlet end of the chamber.

In the above discussion, the chamber has been considered as being disposed horizontally. However, the chamber may be disposed along any direction or having any angle with respect to the horizontal plane. In these cases, we would still consider forces acting on the matter to be discriminated primarily along the direction normal to the traveling direction of the carrier medium. The difference between these cases and the above case where the chamber is disposed horizontally is that the effect of the gravitational force may be different. In the above case, the gravitational force acts in a direction perpendicular to the traveling direction of the carrier medium. In the cases where the chamber is not disposed horizontally, the gravitational force may act in a direction not perpendicular to the traveling direction of the carrier medium. Thus, only a component of the gravitational force should be considered for analyzing the forces exerting on the matter to be discriminated along a direction perpendicular to the traveling direction of the carrier medium.

The velocity profile in the rectangular chamber shown in FIG. 5 depends on the structural characteristics of the chamber. When the chamber length and width is substantially larger than the chamber height, a parabolic or near-parabolic velocity profile along the vertical direction exits in the chamber. The reason for being "near-parabolic" is that the velocity profile at the positions close to the gasket walls does not follow the "parabolic profile". When the chamber width and the chamber height are of similar sizes, the velocity of the carrier medium in the chamber will follow other velocity profile than the "parabolic velocity profile" discussed above. Furthermore, the top and the bottom walls have been considered as flat and parallel to each other during the above discussions. When the top wall and/or the bottom wall are not flat, or when the top wall and the bottom wall are not parallel to each other, or when the top wall or the bottom wall is modified with structures elements of various thickness, the velocity profile of the carrier medium will be different from the "near-parabolic velocity profile" described above.

To produce different velocity profile of the carrier medium, the gasket 230 between the top wall 210 and the bottom wall 220 may be cut in the middle to form channels of other shapes. For example, the channel in the acoustic-E-FFF chamber may have an ellipse shape, similar to that shown in FIG. 2 for an acoustic-FFF chamber. When a carrier medium is caused to travel through such a chamber, the velocity profile of the carrier medium will be different from that for the chamber shown in FIG. 5. Similarly, the channel for the acoustic-FFF chamber shown in FIG. 3 may be used for an acoustic-E-FFF chamber. Such a chamber will result in a unique velocity profile for the carrier medium when it is caused to travel through the channel.

The above discussion of the acoustic-E-FFF chamber has focused on the discrimination of particles where we ignored the influence of thermal diffusion effects. For matter of small sizes to be discriminated in an acoustic-E-FFF chamber, it may be necessary to take into account the thermal diffusion forces. In such cases, the position of the matter being displaced along a direction or within a velocity profile by the applied forces refers to the distribution of the matter that has been influenced by the applied forces. Such distributions of the matter along a direction or within a velocity profile refer to the concentration profile or distribution profile of the matter along the direction or within the velocity profile.

The acoustic-E-FFF chamber may have one or more inlet ports through which the matter to be discriminated and the carrier medium are introduced. The chamber may have one or more outlet ports through which the discriminated matter and the carrier medium may exit the chamber. The inlet and outlet ports may be located on the top or/and bottom walls of the chamber. The inlet and outlet ports may be holes (as small as from about several microns or as large as about several mm in diameter) drilled on the chamber top and/or bottom walls. PEEK or plastic, or metal tubing may be inserted into the holes and serve as the fluid connection between the chamber and the external fluid-circuits such as infusion devices or collection devices. Alternatively, the inlet and outlet port may be a slot (from about micron(s) to about mm in width) drilled across the chamber outlet end. Multiple tubing, arranged in a ribbon form, can be interfaced with such slots. The exemplary acoustic-FFF chamber shown in FIG. 4 could be used as an example for an acoustic-E-FFF chamber. In this case, a single inlet port—a hole—is located at the bottom wall of the chamber. The two outlet ports 180 and 190, positioned at both the top and the bottom walls, are the thin slots cut at the walls. A plurality of tubing arranged in a ribbon form is used to connect to the thin slots as the outlet ports. The two outlet ports arranged at the bottom and top walls correspond to the split-configuration employed in many field-flow-fractionation devices (Springston et al, 1987; Lee et al, 1989; Levin and Giddings, 1991).

B.3. Acoustic-DEP-FFF Chamber.

Figure 7:
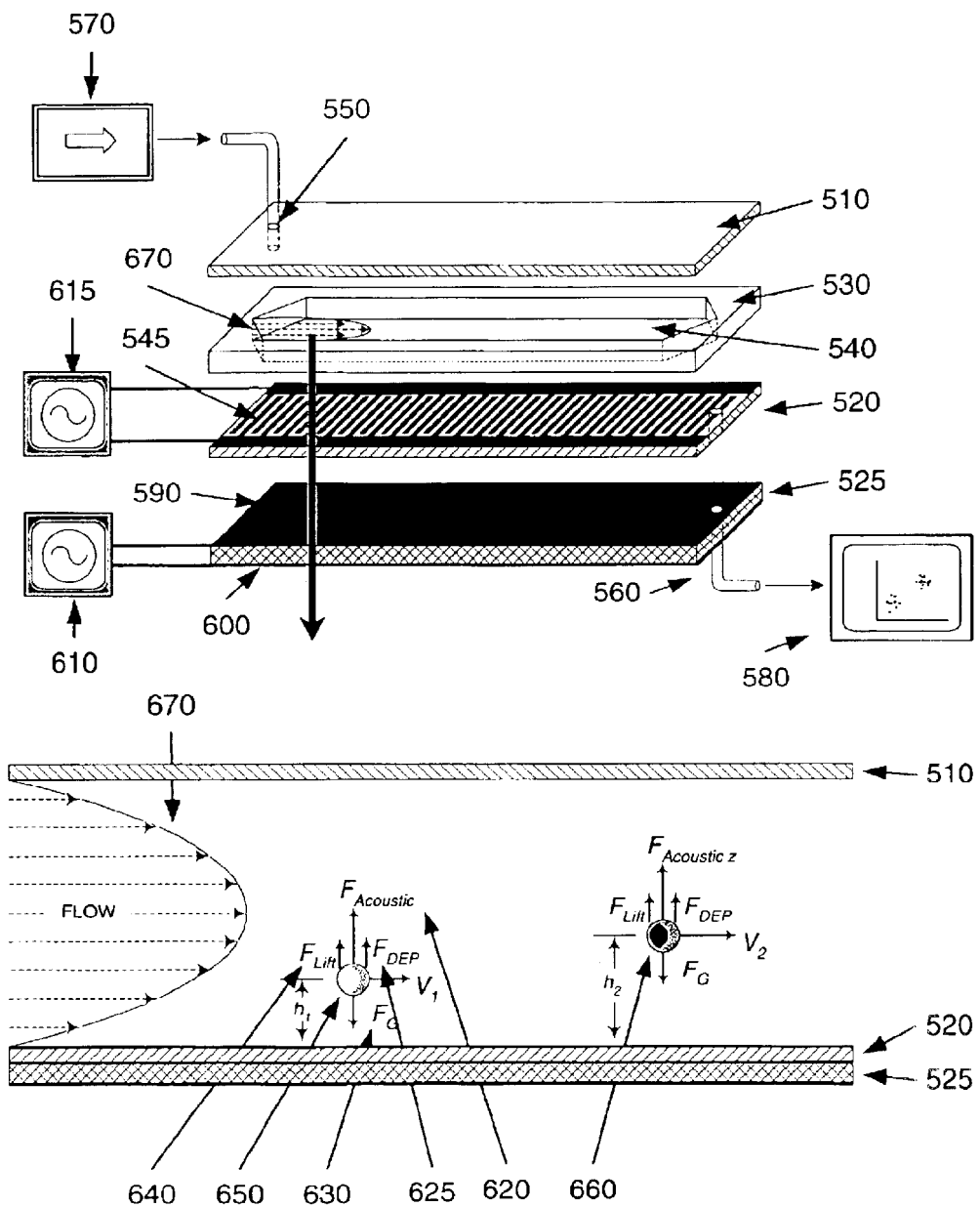
FIG. 7. Schematic diagram of a acoustic-DEP-FFF chamber with a rectangular channel cut in the middle. Also shown is the operation principle of the acoustic-DEP-FFF.

FIG. 7 shows an embodiment of acoustic-DEP-FFF chamber and the operational principle of acoustic-DEP-FFF. The chamber has a top wall 510 and a bottom wall 520. The top wall and bottom wall are separated by a gasket or spacer 530 that has a rectangular channel 540 cut in it. The channel 540 has tapered ends. Under the bottom wall, there is a piezoelectric transducer 525. For clarity, the top wall 510, the gasket 530, the bottom wall 520, and the piezoelectric transducer 525 are shown separated from each other. In use, these components are bound to each other to form an acoustic-DEP-FFF chamber. An inlet port 550 and an outlet port 560 are located on the top wall and bottom wall, at the inlet end and outlet end of the chamber, respectively. The inlet port 550 is connected with an infusion device 570 that can introduce carrier medium and introduce the matter to be discriminated into the chamber. The infusion device may be a syringe pump coupled with an injection valve (Wang et al., 1998; Huang et al., 1999; Yang et al., 1999). The outlet port 560 is connected with a collection or characterization device 580 that is capable of characterizing the matter that has been separated and discriminated after the acoustic-DEP-FFF process. The collection or characterization device may be a particle counter, a flow cytometer or a fractionation collector.

In the exemplary FIG. 7, the piezoelectric transducer 525 has the same size as the entire area of the chamber bottom wall. The top surface 590 and bottom surface 600 of the piezoelectric transducer 525 has been coated with metal films or other electrically conductive material. AC electrical signals from a signal generator 610 can be applied to the top surface 590 and bottom surface 600 of the piezoelectric transducer 525 to energize the piezoelectric transducer so to produce an acoustic wave in the chamber in the direction normal to the surfaces 590 and 600. The acoustic wave transmitted from the piezoelectric transducer is coupled through the bottom wall 520 into the chamber and is reflected back by the top wall 510. The superimposition of the transmitted wave from the piezoelectric transducer and the reflected wave from the top wall form the total acoustic wave field in the chamber. The total acoustic wave field may have two components, i.e., standing-wave component and traveling wave component. The ratio of the magnitude of the standing-wave component to the magnitude of the traveling-wave component is determined by the chamber height (i.e. the distance between the top wall and bottom wall), the wavelength of the acoustic wave, the acoustic properties of the top wall 510 and the bottom wall 520 and the piezoelectric transducer 525, the decaying factor for the acoustic wave in the carrier medium. In one embodiment, the chamber height between the top wall and bottom wall is half wavelength of the standing acoustic wave, and a standing acoustic wave is established in the chamber. An acoustic pressure node exists at the center plane of the chamber. In another embodiment, the chamber height is larger or smaller than half wavelength of the standing acoustic wave.

In the example of FIG. 7, a piezoelectric transducer 525 is bound to the chamber bottom wall 520. There may be many variations in adapting one or more piezoelectric transducers along the portions of the chamber. The piezoelectric transducers may be adapted on the top and/or the bottom walls. For adapting the piezoelectric transducer on the top wall, the transducer may be bound to a solid plate from the top side so that the solid plate forms the top wall of the chamber. The acoustic wave may be generated from the piezoelectric transducer and be coupled into the carrier medium placed in the chamber through the solid plate. Alternatively, the piezoelectric transducer may be used directly as the top wall. For adapting the piezoelectric transducer on the bottom wall, the transducer may be used directly as the chamber bottom wall. The microelectrode elements or arrays may be fabricated directly on the top surface of such piezoelectric transducers. The acoustic-DEP-FFF chamber shown in FIG. 7 comprises one piezoelectric transducer in the chamber. Multiple piezoelectric transducers may be employed in one chamber. These transducers may be adapted on the top wall in series, or on bottom wall in series, or on both top and bottom walls to form a piezoelectric transducer array. The multiple piezoelectric transducers may be energized by same or different electrical signals to produce acoustic waves in the chamber.

In the exemplary FIG. 7, electrode elements employed for generating an electric field in the chamber correspond to the electrode array 545 on the top surface of the bottom wall 520. AC signals may be applied from signal generator 615 across the electrode array 545 to produce a non-uniform electric field in the chamber. The matter being introduced into such a non-uniform electric field will experience dielectrophoretic forces that depend on the dielectric properties of the matter and the medium surrounding the matter and depend on the field non-uniform distributions.

Figure 8:
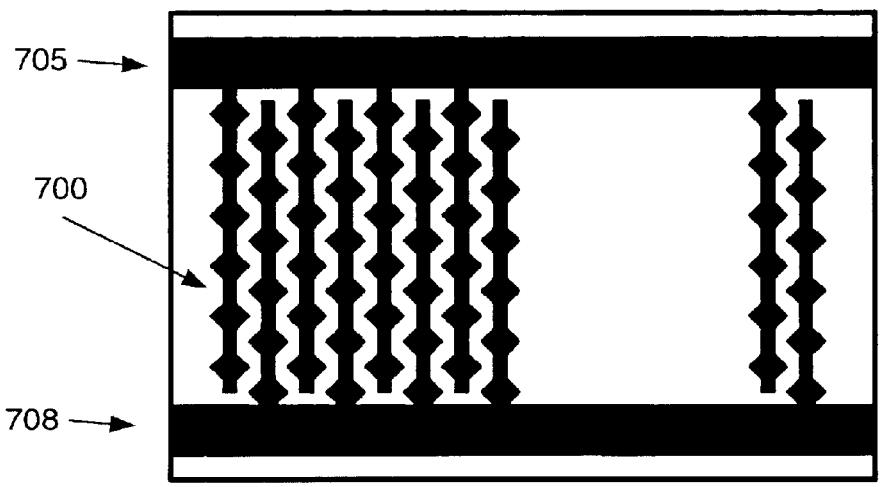
FIG. 8. Schematic diagrams for electrode arrays that may be used for acoustic DEP-FFF apparatus. (A) The interdigitated electrode array with periodic triangular-shaped tips on the electrode elements. (B) The interdigitated electrode array with periodic arc-shaped tips on the electrode elements.
Figure 8:
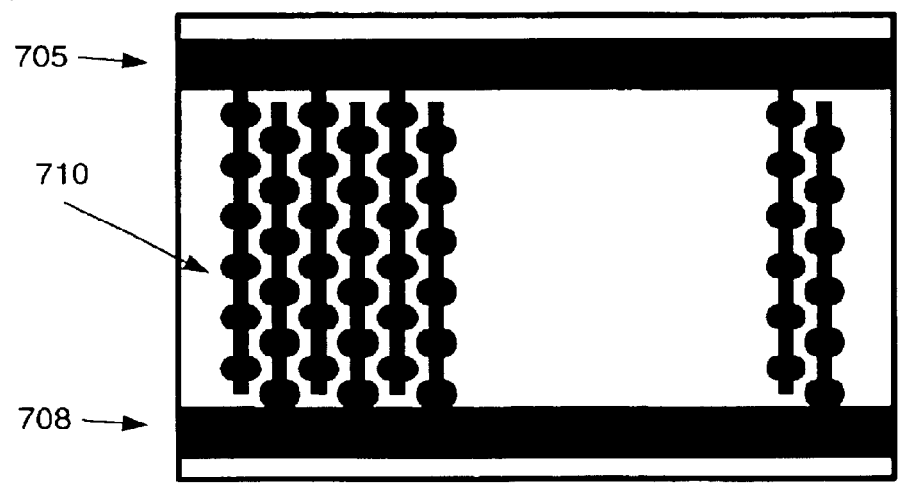

In the example shown in FIG. 7, the electrode array 545 is supported on the top surface of the bottom wall 520 for generating non-uniform electric field. In general, the electrode elements for generating the electric field may be covering only portions of the bottom surface of the top wall, or the portions of the top surface of the bottom wall, or both. Electrode arrays of different configurations may be utilized on these surfaces (i.e., the bottom surface of the top wall or the top surface of the bottom wall). The interdigitated electrode array 400 and an interdigitated castellated electrode array 410 in FIGS. 6A and 6B may be used. The electrode elements may be adapted substantially latitudinally (as shown in FIG. 6A or 6B, or as shown in FIG. 7 for the electrode elements in the array 545) or longitudinally (i.e., the electrode elements in FIG. 6A are turned by 90 degree, or the electrode elements in the array 545 of FIG. 7 are turned by 90 degree) along a portion of the chamber. Similarly, the interdigitated electrode arrays with periodic triangular (700) or arc-like electrode tips (710) shown in FIG. 8 may also be used. The electrode elements may be adapted substantially latitudinally (as shown in FIG. 8A or 8B) or longitudinally (i.e., the electrode elements in FIGS. 8A and 8B are turned by 90 degree) along a portion of the chamber. Individual electrode elements in these electrode arrays shown FIG. 8A and FIG. 8B are connected to one of two common electrical conductor buses 705 and 708. Electrode elements are energized to produce electric fields when electrical signals from signal sources are connected to such electrical conductor buses.

The example shown in FIG. 7 has the configuration that the electrode array 545 is supported on the chamber bottom wall 520 and the piezoelectric transducer 525 is bound to the bottom wall 520. In other embodiments, electrode arrays of various geometrical types may also be fabricated directly on piezoelectric transducers. For example, PZT is a type of piezoelectric material and could be used as a piezoelectric transducer. After its surface being polished to sufficient smoothness, microfabrication methods could be used to fabricate microelectrodes on such piezoelectric substrate. In constructing an acoustic-DEP-FFF chamber operation, the piezoelectric transducer with microelectrodes on the top surface and a planner electrode on the bottom surface may be used as bottom wall of the acoustic-DEP-FFF chamber. The electrical signals could be applied to microelectrode array on the top surface of the piezoelectric transducer to produce dielectrophoresis forces. Simultaneously, electrical signals could be applied to the top array (e.g. through one of the common electrical conductor buses 705 or 708) and the bottom planer electrodes for producing acoustic field and forces. The advantage of this approach is that the electrode array for producing dielectrophoresis forces is integrated onto the surface of the piezoelectric transducer. Such an integration of the electrode array with the piezoelectric transducer is similar to that of the acoustic-E-FFF chamber shown in FIG. 5, where the electrode element for producing electrophoresis force is on the top surface of the piezoelectric transducer.

The matter being introduced into an acoustic-DEP-FFF chamber will experience different forces in the chamber. We consider the case that the matter introduced is microscopic particles and the chamber is disposed horizontally. Referring to FIG. 7 these forces are:

Acoustic radiation force $F_{acoustic}$ 620 in the vertical direction pointing towards or away from the top (or bottom) wall, depending on a factor which relates to the densities of the particles and the suspending medium, and to the acoustic impedance of the of the particles and the medium. The force $F_{acoustic}$ 620 may be a component of total acoustic force acting on the particle.

Dielectrophoretic force $F_{DEP}$ 625 in the vertical direction on the polarized particles. Depending on whether the particles are more or less polarizable than the surrounding medium, this force points downwards to the electrode elements or upwards away from the electrode elements. The dielectrophoretic force $F_{DEP}$ 625 may be a component of the total dielectrophoretic force acting on particles.

Gravitational force $F_G$ 630 levitating or sedimenting the particles, depending on the relative magnitude of the densities of the particles and the suspending medium.

Hydrodynamic lifting force $F_{lift}$ 640 that tends to drive the particles away from the chamber walls. Various theoretical and experimental studies have been conducted on such hydrodynamic forces yet its nature remains in question (Williams et al., 1992; 1994; 1996; 1997). However, it is generally accepted that this force plays an important role only when the particles are very close to the chamber walls (e.g.: <5 micrometer in a chamber of 200 micrometer thick). Some recent work in DEP-FFF (Huang et al., 1997; Wang et al., 1998) shows that this force plays little role in DEP-FFF operation.

These forces are acted on the particles, driving the particles towards equilibrium positions at which these forces balance so that the net force acting on individual particles in the vertical direction is zero, i.e., $$F_{acoustic}(z) + F_{lift}(Z) + F_{DEP}(Z) - F_G = 0$$

Particles of different properties (e.g.: size, geometrical shape, density, dielectric properties, acoustic impedance) equilibrate to different height positions. For example, particles 650 and 660 are displaced to different heights ($h_1$ and $h_2$) from the chamber bottom wall. When a fluid flow is introduced by infusing the carrier medium through inlet port 550 into the chamber, a flow velocity profile 670 is generated. The traveling direction in this case is parallel to the chamber top and bottom walls, and points from the chamber inlet end towards the chamber outlet end. The carrier medium at various positions of the chamber exhibit different velocities. For the example shown in FIG. 7, when the chamber length (i.e., the length of the channel cut in the middle) and chamber width (i.e., the width of the channel) is substantially greater than the chamber height (i.e., the distance between the top wall and bottom wall), the velocity of the carrier medium at the positions not close to the channel walls defined by the gasket follows an approximate parabolic velocity profile in the vertical direction, $$V_m = 6 \langle V_m \rangle \frac{z}{H} \left(1 - \frac{z}{H}\right)$$

where $V_m$ is the velocity of the medium at a height z from the chamber bottom wall, $\langle V_m \rangle$ is the average velocity of the medium, H is the chamber height. Thus, a near-parabolic velocity profile is established along the vertical direction for the carrier medium in such a chamber. Thus, particles 550 and 560 may be discriminated according to the height positions ($h_1$ versus $h_2$) along a vertical direction that is normal to the traveling direction of the carrier medium. Furthermore, because of the velocity profile, the particles 550 and 560 may be further discriminated according to the vertical positions within the velocity profile. Even furthermore, the particles 550 and 560 are caused to travel across the chamber at different velocities $V_1$ and $V_2$. If the particles 550 and 560 are introduced into the chamber at similar time, the particles 550 and 560 will exit the chamber at different times because they are transported through the chamber at different velocities ($V_1$ versus $V_2$). The particles of different properties (e.g.: size, density, geometry, charge, acoustic impedance) may be displaced to different positions along the vertical direction; may be discriminated according to their displacement positions along the vertical direction or within the velocity profile ($h_1$ versus $h_2$); maybe discriminated according to the velocities at which the particles travel through the chamber ($V_1$ versus $V_2$) or according to the exit times of the particles leaving the chamber. Particles of different properties may be fractionated into subpopulations. Alternatively, particles displaced to different heights may be fractionated into sub-populations as they exit the chamber through different outlet ports if the different outlet ports are arranged vertically along the outlet end of the chamber.

In the above discussion, the chamber has been considered as being disposed horizontally. However, the chamber may be disposed along any direction or having any angle with respect to the horizontal plane. In these cases, we would still consider forces acting on the matter to be discriminated primarily along the direction normal to the traveling direction of the carrier medium. The difference between these cases and the above case where the chamber is disposed horizontally is that the effect of the gravitational force may be different. In the above case, the gravitational force acts in a direction perpendicular to the traveling direction of the carrier medium. In the cases where the chamber is not disposed horizontally, the gravitational force may act in a direction not perpendicular to the traveling direction of the carrier medium. Thus, only a component of the gravitational force should be considered for analyzing the forces exerting on the matter to be discriminated along a direction perpendicular to the traveling direction of the carrier medium.

The velocity profile in the rectangular chamber shown in FIG. 7 depends on the structural characteristics of the chamber. When the chamber length and width is substantially larger than the chamber height, a parabolic or near-parabolic velocity profile along the vertical direction exits in the chamber. The reason for being "near-parabolic" is that the velocity profile at the positions close to the gasket walls does not follow the "parabolic profile". When the chamber width and the chamber height are of similar sizes, the velocity of the carrier medium in the chamber will follow other velocity profile than the "parabolic velocity profile" discussed above. Furthermore, the top and the bottom walls have been considered as flat and parallel to each other during the above discussions. When the top wall and/or the bottom wall are not flat, or when the top wall and the bottom wall are not parallel to each other, or when the top wall or the bottom wall is modified with structures elements of various thickness, the velocity profile of the carrier medium will be different from the "near-parabolic velocity profile" described above.

To produce different velocity profile of the carrier medium, the gasket 530 between the top wall 510 and the bottom wall 520 may be cut in the middle to form channels of other shapes. For example, the channel in the acoustic-DEP-FFF chamber may have an ellipse shape, similar to that shown in FIG. 2 for an acoustic-FFF chamber. When a carrier medium is caused to travel through such a chamber, the velocity profile of the carrier medium will be different from that for the chamber shown in FIG. 7. Similarly, the channel for the acoustic-FFF chamber shown in FIG. 3 may be used for an acoustic-DEP-FFF chamber. Such a chamber will result in a unique velocity profile for the carrier medium when it is caused to travel through the channel.

The above discussion of the acoustic-DEP-FFF chamber has focused on the discrimination of particles where we ignored the influence of thermal diffusion effects. For matter of small sizes to be discriminated in an acoustic-DEP-FFF chamber, it may be necessary to take into account the thermal diffusion forces. In such cases, the position of the matter being displaced along a direction or within a velocity profile by the applied forces refers to the distribution of the matter that has been influenced by the applied forces. Such distributions of the matter along a direction or within a velocity profile refer to the concentration profile or the distribution profile of the matter along the direction or within the velocity profile.

The acoustic-DEP-FFF chamber may have one or more inlet ports through which the matter to be discriminated and the carrier medium are introduced. The chamber may have one or more outlet ports through which the discriminated matter and the carrier medium may exit the chamber. The inlet and outlet ports may be located on the top or/and bottom walls of the chamber. The inlet and outlet ports may be holes (as small as from about several microns or as large as about several mm in diameter) drilled on the chamber top and/or bottom walls. PEEK or plastic, or metal tubing may be inserted into the holes and serve as the fluid connection between the chamber and the external fluid-circuits such as infusion devices or collection devices. Alternatively, the inlet and outlet port may be a slot (from about micron(s) to about mm in width) drilled across the chamber outlet end. Multiple tubing, arranged in a ribbon form, can be interfaced with such slots. The exemplary acoustic-FFF chamber shown in FIG. 4 could be used as an example for an acoustic-DEP-FFF chamber. In this case, a single inlet port—a hole—is located at the bottom wall of the chamber. The two outlet ports 180 and 190 in FIG. 4, positioned at both the top and the bottom walls, are the thin slots cut at the walls. A plurality of tubing arranged in a ribbon form is used to connect to the thin slots as the outlet ports. The two outlet ports arranged at the bottom and top walls correspond to the split-configuration employed in many field-flow-fractionation devices (Springston et al, 1987; Lee et al, 1989; Levin and Giddings, 1991).

C. Exemplary Methods

C.1. Batch-Mode Operation for Acoustic-FFF, Acoustic-E-FFF and Acoustic-DEP-FFF.

Figure 9:
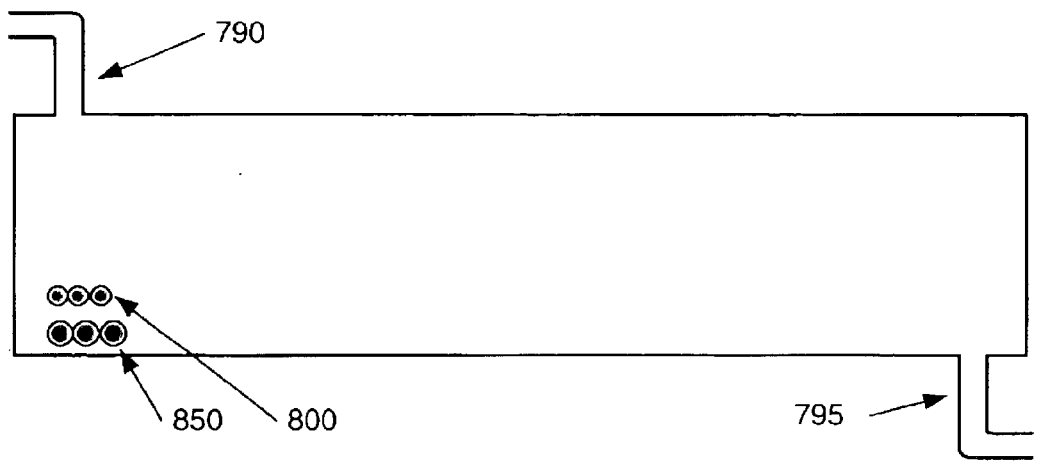
FIG. 9. Schematic diagram showing the "batch mode operation principle" for using acoustic-FFF, acoustic-E-FFF and acoustic-DEP-FFF apparatuses. (A) Different types of particles are displaced to different equilibrium height positions under the influence of the applied forces during the "relaxation" process. (B) The particles that have been displaced to different equilibrium positions move along the chamber at different velocities under influence of an established fluid flow in the chamber.
Figure 9:
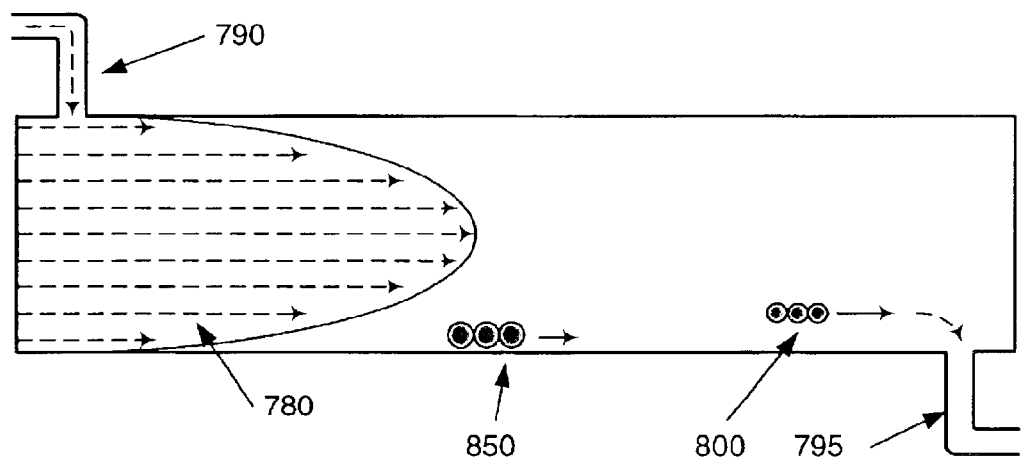

In the batch-mode operation, an acoustic-FFF (or acoustic-E-FFF or acoustic-DEP-FFF) chamber is preloaded with a carrier medium through the inlet port. Particle-mixture samples (e.g. 100 $\mu$L) are then delivered, e.g. injected or otherwise introduced into the medium in the chamber through the inlet port. For acoustic-FFF, appropriate acoustic field condition is applied so that particles are given a specified time to reach their equilibrium positions under the influence of the acoustic force and other forces (e.g., gravitational force, hydrodynamic lifting force). The acoustic field conditions in the chamber(s) are applied through energizing the piezoelectric transducer(s) with appropriate electrical signals. For acoustic-E-FFF, appropriate electric field and acoustic field conditions are applied so that particles are given a specified time to reach their equilibrium positions under the influence of the acoustic force, electrophoretic force and other forces (e.g., gravitational force, hydrodynamic lifting force). For acoustic-DEP-FFF, appropriate dielectrophoretic field and acoustic field conditions are applied so that particles are given a period of time to reach their equilibrium positions under the influence of the acoustic force, dielectrophoretic force and other forces (e.g., gravitational force, hydrodynamic lifting force). This step is called the "relaxation" in typical field-flow-fractionation (Giddings, 1981, Giddings, 1993). During the relaxation step (FIG. 9A), particles of different properties are displaced to different equilibrium positions within the chamber under the influence of applied forces. For particles (or matter) of small sizes where the thermal diffusion effect plays role in particle equilibrium positions, the equilibrium positions of different particle types correspond to the equilibrium concentration profile for different particle types. Following the relaxation process, fluid flow is then established and particles at different heights are driven to move through the chamber at different velocities. In this process, the externally applied field conditions are maintained. Particles of different properties are separated into fractions according to the time they exit the chamber (FIG. 9B). FIGS. 9A and 9B show such a batch-mode process in a cross-sectional view of a rectangular, acoustic-FFF (or acoustic-E-FFF, or acoustic-DEP-FFF) chamber. FIG. 9A shows that during the relaxation step, particle types 800 and 850 have been displaced to different heights under the influence of the applied forces. FIG. 9B shows that after the fluid flow profile (i.e., a velocity profile 780) is established in the chamber following the relaxation step, particle type 800 has moved ahead of particle type 850 and will exit the chamber earlier at the outlet port 795 The fluid flow is established by infusing a carrier medium into the chamber inlet port 790.

Batch-mode is the typical mode of operation for most field-flow-fractionation.

Particles can exit the chamber from a single outlet port or multiple outlet ports (e.g. one on the top and one on the bottom wall). The two-outlet-ports located at the top and bottom walls may be used to collect two separated fractions directly. The "relaxation" step may not be necessary in some applications. Depending on the type of particle mixtures, it is possible that particles will attain their equilibrium height positions during the fluid flow shortly after being introduced into the chamber. In this case, particles can be separated in a batch mode without the need of "relaxation step".

Thus, the "batch-mode" operation of discriminating a matter using acoustic force in field flow fractionation comprises the following steps: a) obtaining an acoustic-FFF apparatus described in this invention; b) loading a carrier medium into the chamber of apparatus via its inlet port until the chamber is filled with the carrier medium; c) delivering a sample that contains a matter to be discriminated into the carrier medium in the chamber; d) applying at least one electrical signal provided by an electrical signal generator to the piezoelectric transducer, wherein said energized piezoelectric transducer creates an acoustic wave, thereby causing at least one acoustic force on said matter; e) introducing the carrier medium into the chamber of the apparatus via its inlet port, wherein said introducing causes the carrier medium to travel through the chamber according to a velocity profile; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. This "batch-mode" acoustic-FFF can be used with any acoustic-FFF apparatus described in this invention.

In the above "batch-mode" method of acoustic-FFF, preferably, prior to the introducing of carrier medium into the chamber that causes the carrier medium to travel through the chamber according to a velocity profile (i.e., prior to step e), the matter to be discriminated is displaced into equilibrium position along a direction normal to the traveling direction of the carrier medium traveling through the chamber by applying electrical signal to the piezoelectric transducer to cause acoustic force on said matter.

The "batch-mode" operation of discriminating a matter using electrophoretic and acoustic forces in field flow fractionation comprises the following steps: a) obtaining an acoustic-E-FFF apparatus described in the present invention; b) loading a carrier medium into the chamber of apparatus via its inlet port until the chamber is filled with the carrier medium; c) delivering a sample that contains a matter to be discriminated into the carrier medium in the chamber; d) applying at least one electrical signal provided by an electrical signal generator to the electrode element, wherein said energized electrode element creates an electrical field, thereby causing at least one electrophoretic force on said matter; e) applying at least another electrical signal provided by an electrical signal generator to the piezoelectric transducer, wherein said energized piezoelectric transducer creates an acoustic wave, thereby causing at least one acoustic force on said matter; f) introducing the carrier medium into the chamber of the apparatus via its inlet port, wherein said introducing causes the carrier medium to travel through the chamber according to a velocity profile; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. Any of the acoustic-E-FFF apparatus described in the present invention can be used in the "batch-mode" operation of acoustic-E-FFF.

In the above described "batch-mode" of acoustic-E-FFF method, preferably, prior to the introducing of carrier medium into the chamber that causes the carrier medium to travel through the chamber according to a velocity profile (i.e., prior to step f), the matter to be discriminated is displaced into equilibrium position along a direction normal to the traveling direction of the carrier medium traveling through the chamber applying by applying electrical signal to the electrode element to cause electrophoretic force on said matter and applying electrical signal to the piezoelectric transducer to cause acoustic force on said matter.

The "batch-mode" operation of discriminating a matter using dielectrophoretic and acoustic forces in field flow fractionation comprises the following steps: a) obtaining an acoustic-DEP-FFF apparatus described in the present invention; b) loading a carrier medium into the chamber of apparatus via its inlet port until the chamber is filled with the carrier medium; c) delivering a sample that contains a matter to be discriminated into the carrier medium in the chamber, d) applying at least one electrical signal provided by an electrical signal generator to the electrode element, wherein said energized electrode element creates a non-uniform electrical field, thereby causing at least one dielectrophoretic force on said matter; e) applying at least another electrical signal provided by an electrical signal generator to the piezoelectric transducer, wherein said energized piezoelectric transducer creates an acoustic wave, thereby causing at least one acoustic force on said matter; f) introducing the carrier medium into the chamber of the apparatus via its inlet port, wherein said introducing causes the carrier medium to travel through the chamber according to a velocity profile; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. Any of the acoustic-DEP-FFF apparatuses described in the present invention can be used in the "batch-mode" operation of acoustic-DEP-FFF.

In the above described "batch-mode" of acoustic-DEP-FFF method, preferably, prior to the introducing of carrier medium into the chamber that causes the carrier medium to travel through the chamber according to a velocity profile (step f), the matter to be discriminated is displaced into equilibrium position along a direction normal to the traveling direction of the carrier medium traveling through the chamber by applying electrical signal to the electrode element to cause dielectrophoretic force on said matter and applying electrical signal to the piezoelectric transducer to cause acoustic force on said matter.

In the above acoustic-E-FFF or acoustic-DEP-FFF methods, identical, but preferably, different electric signals are used to generate the acoustic force and the electrophoretic or the dielectrophoretic force.

In the above acoustic-E-FFF or acoustic-DEP-FFF method, the acoustic force and the electrophoretic or the dielectrophoretic force can be generated simultaneously or sequentially.

C.2. Continuous mode operation for acoustic-FFF, acoustic-E-FFF and acoustic-DEP-FFF.

In the continuous-mode operation, particle-mixture samples are continuously fed into the acoustic-FFF (or acoustic-E-FFF or acoustic-DEP-FFF) chamber through the inlet port. For acoustic-FFF, appropriate acoustic field condition is applied so that particles that are continuously fed into the chamber are continuously being driven towards their equilibrium positions under the influence of the acoustic force and other forces (e.g. gravity, hydrodynamic lift force). The acoustic field conditions in the chamber(s) are applied through energizing the piezoelectric transducer(s) with appropriate electrical signals. For acoustic-E-FFF, appropriate electric field and acoustic wave conditions are applied so particles that are continuously fed into the chamber are continuously being driven towards their equilibrium positions under the influence of the acoustic force, electrophoretic force and other forces (e.g. gravity, hydrodynamic lift force). For acoustic-DEP-FFF, appropriate dielectrophoretic field and acoustic wave conditions are applied so that particles that are continuously fed into the chamber are continuously being driven towards their equilibrium positions under the influence of the acoustic force, dielectrophoretic force and other forces (e.g. gravity, hydrodynamic lift force). Take a particle-mixture consisting of two subpopulations as an example to be separated or analyzed in an acoustic-FFF (or acoustic-E-FFF, or acoustic-DEP-FFF) chamber. The subpopulation having higher equilibrium positions in the acoustic-FFF (or acoustic-E-FFF, or acoustic-DEP-FFF) chamber may exit the chamber from an outlet port that is located at higher positions at the outlet end. The subpopulations having lower equilibrium positions may exit the chamber from an outlet port that is located at lower positions at the outlet end. Thus particle mixtures can be continuously separated into two fractions. Clearly, split-flow at the chamber outlet end is needed (Springston et al, 1987; Lee et al, 1989; Levin and Giddings, 1991).

Figure 10:
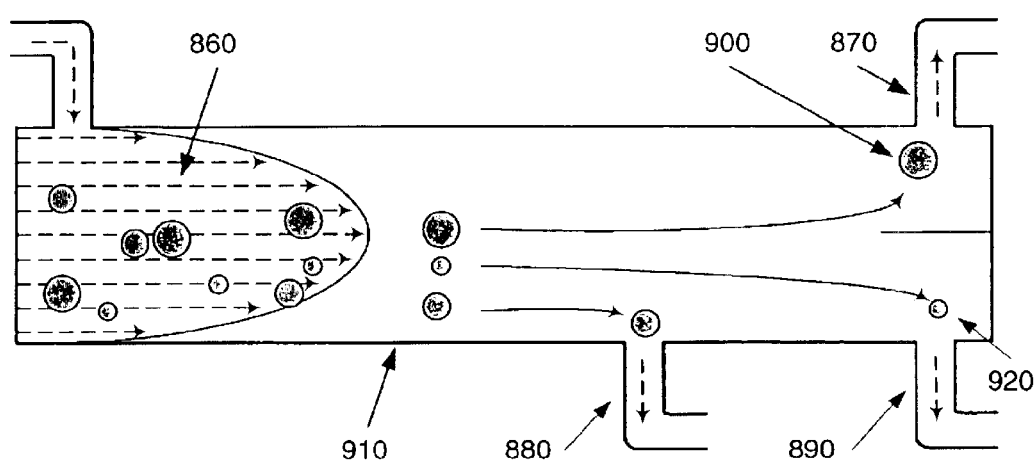
FIG. 10. Schematic diagram showing the "continuous mode operation principle" for using acoustic-FFF, acoustic-E-FFF and acoustic-DEP-FFF apparatuses. Particles in a carrier medium are continuously fed into the chamber, are continuously displaced to different height positions in the carrier medium and exit the chamber at different outlet ports.

Multiple fractions can be collected if multiple outlet ports are located at either the top or the bottom or both walls for a chamber having top and bottom walls. FIG. 10 shows an example where the chamber has one outlet port 870 on the top wall and two outlet ports 880 and 890 on the bottom wall. Such a chamber can be used to separate particle mixture having three (or more than three) subpopulations. The chamber may be an acoustic-FFF chamber, or acoustic-E-FFF chamber, or acoustic-DEP-FFF chamber. A fluid velocity profile (i.e. fluid flow profile) 860 is established in the chamber. The subpopulation 900 that is displaced to the highest positions by the applied forces during the transit time through the chamber may exit the outlet port 870 at the top wall. The subpopulation 910 that is displaced to the lowest positions by the applied forces during the transit time through the chamber may exit the chamber from the first outlet port 880 on the bottom wall. The subpopulation 920 that is displaced to the middle heights may exit the chamber from the second outlet port 890 on the bottom wall. Such continuous operation corresponds to the procedure for the FFF systems with split-configurations (Springeston et al, 1987; Lee et al, 1989; Levin and Giddings, 1991).

Thus, "continuous-mode" operation of discriminating a matter using acoustic forces in field flow fractionation comprises the following steps: a) obtaining an acoustic-FF apparatus described in the present invention; b) introducing a carrier medium containing a matter to be discriminated into the chamber of the apparatus via its inlet port, wherein said introducing causes the carrier medium to travel through the chamber according to a velocity profile; c) applying at least one electrical signal provided by an electrical signal generator to the piezoelectric transducer, wherein said energized piezoelectric transducer creates an acoustic wave, thereby causing at least one acoustic force on said matter having components normal to the traveling direction of said carrier medium travelling through said chamber; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. The continuous mode of acoustic-FFF can be used with any acoustic-FFF apparatus described in this invention.

The "continuous-mode" operation of discriminating a matter using electrophoretic and acoustic forces in field flow fractionation comprises the following steps: a) obtaining an acoustic-E-FFF apparatus described in the present invention; b) introducing a carrier medium containing a matter to be discriminated into the apparatus via its inlet port, wherein said introducing causes the carrier medium to travel through the chamber according to a velocity profile; c) applying at least one electrical signal provided by an electrical signal generator to the electrode elements, wherein said energized electrode elements creates an electrical field, thereby causing at least one electrophoretic force on said matter having components normal to the traveling direction of said carrier medium travelling through said chamber; and d) applying at least another electrical signal provided by an electrical signal generator to the piezoelectric transducer, wherein said energized piezoelectric transducer creates an acoustic wave, thereby causing at least one acoustic force on said matter having components normal to the traveling direction of said carrier medium travelling through said chamber; whereby said matter is displaced to a position within said carrier medium along a direction normal to the traveling direction of said carrier medium travelling through said chamber and discriminated according to its position within said carrier medium along the direction normal to the traveling direction of said carrier medium travelling through said chamber. Any of the acoustic-FFF apparatuses described in the present invention can be used the "continuous-mode" of acoustic-E-FFF.

The "continuous-mode" operation of discriminating a matter using dielectrophoretic and acoustic forces in field flow fractionation comprises the following steps: a) obtaining an acoustic-DEP-FFF apparatus described in the present invention; b) introducing a carrier medium containing a matter to be discriminated into the apparatus via its inlet port, wherein said introducing causes the carrier medium to travel through the chamber of the apparatus according to a velocity profile; c) applying at least one electrical signal provided by an electrical signal generator to the electrode element, wherein said energized electrode element creates a non-uniform electrical field, thereby causing at least one dielectrophoretic force on said matter having components normal to the traveling direction of said carrier medium travelling through said chamber; and d) applying at least another electrical signal provided by an electrical signal generator to the piezoelectric transducer, wherein said energized piezoelectric transducer creates an acoustic wave, thereby causing at least one acoustic force on said matter having components normal to the traveling direction of said carrier medium travelling through said chamber; whereby said matter is displaced to a position within said carrier medium along a direction normal to the traveling direction of the carrier medium traveling through the chamber and discriminated according to its position within said carrier medium along the direction normal to the traveling direction of the carrier medium traveling through the chamber. Any acoustic-DEP-FFF apparatus described in the present invention can be used in the "continuous-mode" operation of acoustic-DEP-FFF.

D. Forces

Although not wish to be bound by any theories and mechanisms described herein, the following illustrates the various forces through which the present apparatuses and methods are used or operated.

D.1. Acoustic Radiation Forces

Acoustic radiation force is a non-contact force that can be used for trapping, handling, moving particles in fluid. The use of the acoustic radiation force in a standing ultrasound wave for particle manipulation has been demonstrated for concentrating erythrocytes (Yasuda et al, 1997), focusing micron-size polystyrene beads (0.3 to 10 micron in diameter, Yasuda and Kamakura, 1997), concentrating DNA molecules (Yasuda et al, 1996C), batch and semicontinuous aggregation and sedimentation of cells (Pui, et al, 1995). By competing electrostatic and acoustic radiation forces, separation of polystyrene beads of different size and charges have been reported (Yasuda et al, 1996A, B). Furthermore, in terms of ion leakage (for erythrocytes, Yasuda et al, 1997) or antibody production (for hybridoma cells, Pui. et al, 1995), little or no damage or harming effect was observed when acoustic radiation force was used to manipulate mammalian cells.

A standing plane, acoustic wave can be established in an acoustic-FFF chamber, or acoustic-E-FFF or acoustic-DEP-FFF chamber by applying AC signals to the piezoelectric transducers. Alternatively, an acoustic wave that has a standing-wave component can be established in an acoustic-FFF chamber, or acoustic-E-FFF or acoustic-DEP-FFF chamber by applying AC signals to the piezoelectric transducers. We will now examine the acoustic radiation force exerting a particle in 1 standing acoustic wave field. Assume that the standing wave is established along a particular direction (e.g., z-axis direction) in a fluid. The standing wave spatially varying along the z axis in the fluid can be expressed as:

$$\Delta p(z) = p_0 \sin(kz) \cos(\omega_a t)$$

where $\Delta p$ is acoustic pressure at z, $p_0$ is the acoustic pressure amplitude, k is the wave number ($2\pi/\lambda$, where $\lambda$ is the wavelength), z is the distance from the pressure node, $\omega$ is the angular frequency, and t is the time. According to the theory developed by Yoshioka and Kawashima (1955), the radiation force $F_{acoustic}$ acting on a spherical particle in the stationary standing wave field is given by (see "Acoustic radiation pressure on a compressible sphere" by K. Yoshioka and Y. Kawashima in Acustica, 1955, Vol. 5, pages 167–173), $$F_{acoustic} = -\frac{4\pi}{3} r^3 k E_{acoustic} A \sin(2kz)$$

where r is the particle radius, $E_{acoustic}$ is the average acoustic energy density, A is a constant given by $$A = \frac{5\rho_p - 2\rho_m}{2\rho_p + \rho_m} - \frac{\gamma_p}{\gamma_m}$$

where $\rho_m$ and $\rho_p$ are the density of the particle and the medium, $\gamma_m$ and $\gamma_p$ are the acoustic impedance of the particle and medium, respectively. A is termed herein as the acoustic-polarization-factor. The acoustic impedance ($\gamma_m$ and $\gamma_p$ for the medium and the particle) of a material is defined as the product between the density ($\rho_1$ and $\rho_p$ for the medium and the particle) of the material and the acoustic velocity ($C_m$ or $C_p$ for the medium and the particle) in the material ($\gamma_m = \rho_m \cdot C_m$ and $\gamma_p = \rho_p \cdot C_p$).

When A>0, the particle moves towards the pressure node (z=0) of the standing wave.

When A<0, the particle moves away from the pressure node.

Clearly, particles having different density and acoustic impedance will experience different acoustic-radiation-forces when they are placed into the same standing acoustic wave field. For example, the acoustic radiation force acting on a particle of 10 micron in diameter can vary somewhere between 0.01 and 1000 pN, depending on the established acoustic energy density distribution.

The paper of "Acoustic radiation pressure on a compressible sphere" by K. Yoshioka and Y. Kawashima published in Acustica, 1955, Vol. 5, pages 167–173 also described a theory for the acoustic radiation forces exerting on a particle in a traveling wave acoustic field. Using such theories, those skilled in the art of acoustic manipulation of particles may readily analyze and calculate the acoustic radiation forces on a particle in a given acoustic field.

The piezoelectric transducers are made from "piezoelectric materials" that produce an electric field when exposed to a change in dimension caused by an imposed mechanical force (piezoelectric or generator effect). Conversely, an applied electric field will produce a mechanical stress (electrostrictive or motor effect) in the materials. They transform energy from mechanical to electrical and vice-versa. The piezoelectric effect was discovered by Pierre Curie and his brother Jacques in 1880. It is explained by the displacement of ions, causing the electric polarization of the materials' structural units. When an electric field is applied, the ions are displaced by electrostatic forces, resulting in the mechanical deformation of the whole material. Thus, in an acoustic-FFF or acoustic-E-FFF or acoustic-DEP-FFF apparatus, when AC voltages are applied to the piezoelectric transducers, the vibration occurred to the transducers will be coupled into the fluid in the chamber and result in an acoustic wave in the chamber. Such an acoustic wave may have standing wave and traveling wave components.

Separation of particles in a medium using acoustic wave has been reported previously. For example, U.S. Pat. No. 4,523,682, which is hereby incorporated by reference in its entirety, discloses a method for separating particles of different sizes, densities and other properties in an acoustic chamber. U.S. Pat. No. 4,523,682 describes the spatial separation of particles of different properties in an acoustic wave. The aspect of acoustic-FFF separation in the present invention provides the apparatus and methods for separating particles from a mixture. The purified particle populations may be obtained using the present invention, while the U.S. Pat. No. 4,523,682 can separate particles only according to the positions the particles occupy in an acoustic chamber.

D.2. Electrophoretic Forces

The electrostatic force or electrophoretic force $F_E$ on a particle in an applied electrical field $E_z \vec{a}_z$ is given by $$F_E = Q_p E_z \vec{a}_z$$

where $Q_p$ is the effective electric charge on the particle. The direction of the electrostatic force (or electrophoretic force) on the charged particle depends on the polarity of the particle charge as well as the applied-field direction.

D.3. Dielectrophoretic Forces

The dielectrophoretic force $F_{DEP_z}$ acting on a particle of radius r subjected to a non-uniform electrical field is given by $$F_{DEP_x} = 2\pi \Sigma_m r^3 \chi_{DEP} \nabla E_{rms}^2 \cdot \vec{a}_z$$

where $E_{rms}$ is the RMS value of the field strength, $\Sigma_m$ is the dielectric permitivity of the medium. $\chi_{DEP}$ is the particle polarization factor, given by $$\chi_{DEP} = Re\left(\frac{\varepsilon_p^* - \varepsilon_m^*}{\varepsilon_p^* + 2\varepsilon_m^*}\right),$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\Sigma_p$ and $\sigma_P$ are the effective permitivity and conductivity of the particle, respectively. These parameters may be frequency dependent. For example, a typical biological cell will have frequency dependent, effective conductivity and permitivity, at least, because of cytoplasm membrane polarization. In the above equation, $F_{DEP_z}$ is the component of total dielectrophoretic force along the direction $\vec{a}_z$. In the present application, the dielectrophoretic (DEP) force refers to the force acting on particles due to electric fields of non-uniform strength. In the literature, such forces were sometimes referred as conventional dielectrophoretic forces. However, in the present application, for the sake of simplicity, we call the forces acting on particles due to electrical fields of non-uniform strength "dielectrophoretic forces" or "DEP forces".

The above equation for the dielectrophoretic force can be also written as $$F_{DEP_z} = 2\pi \Sigma_m r^3 \chi_{DEP} V^2 p(z) \vec{a}_x$$

where p(z) is the square-field distribution for a unit-voltage excitation (V=1 V) on the electrodes, V is the applied voltage.

A non-uniform electrical field can be established in an acoustic-DEP-FFF chamber by applying AC signals to the microelectrodes incorporated on the chamber surfaces. For an interdigitated electrode array, the dielectrophoretic forces will follow an approximately exponential decay with the distance from the electrode plane, as shown by Huang et al, 1997.

Particles or cells having different dielectric property (as defined by permitivity and conductivity) will experience different dielectrophoretic forces in the vertical direction in an acoustic-DEP-FFF chamber. For DEP manipulation of particles (including biological cells), DEP forces acting on a particle of 10 micron in diameter can vary somewhere between about 0.01 and about 1000 pN.

In previously reported DEP-FFF technology (Huang et al, Biophys. J. Vol. 73, p1118–1129, 1997; Wang et al., Biophys. J. Vol. 74, p2689–2701, 1998; Yang, J. et al. Anal. Chem. Vol. 71, p911–918, 1999), only negative DEP forces can be used to influence/control/manipulate particle positions in fluid flow velocity profile because the use of positive DEP may result in the particles being directed and trapped on the electrode elements. However, in the acoustic-DEP-FFF apparatus and acoustic-DEP-FFF method in the present invention, both positive and negative DEP forces can be used since the use of spatially-varying acoustic radiation forces provides additional control for displacing particles in a fluid stream. Positive DEP forces may be balanced by the spatially-varying acoustic radiation forces that are in an opposing direction.

D.4. Hydrodynamic Lifting Forces

A fluid flow profile may be established in an acoustic-FFF chamber, or acoustic-E-FFF or acoustic-DEP-FFF chamber for particle separation and analysis. For a rectangular chamber with the chamber length and chamber width substantially greater than the chamber height, a laminar, parabolic flow profile may be generated. Such a velocity profile may be described as, $$V_m = 6\langle V_m\rangle \frac{z}{H}\left(1 - \frac{z}{H}\right)$$

where $V_m$ is the fluid velocity at the height z from the chamber bottom. H is the chamber height and $\langle V_m\rangle$ is the average fluid-velocity in the chamber. When a particle is carried with the fluid in such a profile, there is a hydrodynamic lifting force ($F_{lift}$) acting on the particle in the vertical direction if the particle is placed close to the chamber bottom (or top) wall and if the chamber is disposed horizontally or nearly-horizontally. If the distance between the particle and the chamber bottom wall is very small (e.g. <1 micron for a 10 micron particle in a 200 micron height chamber), the hydrodynamic lifting force will direct the particle away from the chamber wall (Williams et al., 1992; 1994; 1996; 1997). This force has been used in the classical, hyperlayer-FFF operation in which the particles are positioned at different height from the chamber wall by balancing the hydrodynamic lifting force and sedimentation force (e.g., Ratanathanawongs S. K. and Giddings, 1992, Williams et al, 1996). It is known that this hydrodynamic lifting force decay rapidly to zero with the distance from the chamber wall, yet its origin remains to be debated.

D.5. Force Balance in Acoustic-FFF, Acoustic-E-FFF and Acoustic-DEP-FFF Chambers In an acoustic-FFF chamber that is disposed horizontally or nearly horizontally with a fluid flow along the horizontal direction being established in the chamber, three types of forces are exerted on a particle in the vertical direction, ie., $F_{acoustic}$, $F_{lift}$, and sedimentation forces $$F_G = -\frac{4}{3}\pi r^3 (\rho_p - \rho_m).$$

When these forces are balanced, $$F_{acoustic}(Z) + F_{lift}(Z) + F_G = 0$$

the particle experience no-force and would cease to move up or down. With the position-dependent acoustic and hydrodynamic lifting forces, particles may equilibrate at such zero-force height positions ($h_{eq}$). Such a position is dependent on the applied acoustic wave energy density, and more importantly, particle density and acoustic impedance, and particle size. Particles of different properties (density, acoustic impedance, size) will equilibrate at different heights, and will move at different velocities ($V_p$, dependent on $h_{eq}$) under the influence of the fluid-flow, and will transverse through the chamber at different time ($t_p$=L/$V_p$). Similar analysis can be performed for an acoustic-FFF chamber that is not disposed horizontally. In such a case, the effect of the sedimentation force on the displacement of the particles within the flow velocity profile is different from that shown above. Only a component of the sedimentation force, which is within the velocity profile and is perpendicular to the traveling direction of the carrier medium, contributes to the displacement of the particles in the velocity profile.

In an acoustic-E-FFF chamber that is disposed horizontally or nearly horizontally with a fluid flow along the horizontal direction being established in the chamber, four types of forces are exerted on a particle in the vertical direction, i.e., $F_{acoustic}$, $F_E$, $F_{lift}$, and sedimentation forces $$F_G = -\frac{4}{3}\pi r^3 (\rho_p - \rho_m).$$

When these forces are balanced, $$F_{acoustic}(Z) + F_E + F_{lift}(z) + F_G = 0$$

the particle experience no-force and would cease to move up or down. With the position-dependent acoustic and hydrodynamic lifting forces, particles may equilibrate at such zero-force height positions ($h_{eq}$). Such a position is dependent on the applied acoustic wave energy density, the applied electrical field, and more importantly, particle density and acoustic impeance, particle effective charge and size. Particles of different properties (density, acoustic impedance, effective charge, size) will equilibrate at different heights, and will move at different velocities ($V_p$ dependent on $h_{eq}$) under the influence of the fluid-flow, and will transverse through the chamber at different time ($t_p$=L/$V_p$). Compared with electrical-FFF, the acoustic-radiation-force has been added into the force equation. Similar force-balance analysis can be performed for an acoustic-E-FFF chamber that is not disposed horizontally. In such a case, the effect of the sedimentation force on the displacement of the particles within the flow velocity profile is different from that shown above. Only a component of the sedimentation force, which is within the velocity profile and is perpendicular to the traveling direction of the carrier medium, contributes to the displacement of the particles in the velocity profile.

By competing the acoustic radiation force with electrostatic (electrophoretic) forces, Yasuda et al. (1996A, B) demonstrated the spatial separation of more than 20 micron for polystyrene particles of different sizes and different charges in a chamber of about 750 micron thick.

Similarly, in an acoustic-DEP-FFF chamber that is disposed horizontally or nearly horizontally with a fluid flow along the horizontal direction being established in the chamber, the force balance equation for a particle in the acoustic-DEP-FFF chamber is given by $$F_{acoustic}(z) + F_{DEP}(z) + F_{lift}(z) + F_G = 0$$

Again, the zero-net-force position may correspond to an equilibrium height $h_{eq}$. Such position is dependent on the applied acoustic wave energy density, the applied non-uniform electrical field, and more importantly, particle density, and dielectric property and size. Particles of different properties (density, acoustic impedance, dielectric property, size) will equilibrate at different heights, and will move at different velocities ($V_p$, dependent on $h_{eq}$) under the influence of the fluid-flow, and will transverse through the chamber at different time ($t_p$=L/$V_p$). Compared with DEP-FFF, the acoustic-radiation-force has been added into the force equation. Similar force-balance analysis can be performed for an acoustic-DEP-FFF chamber that is not disposed horizontally. In such a case, the effect of the sedimentation force on the displacement of the particles within the flow velocity profile is different from that shown above. Only a component of the sedimentation force, which is within the velocity profile and is perpendicular to the traveling direction of the carrier medium, contributes to the displacement of the particles in the velocity profile.

The above analysis is based on single (large) particles, and particle diffusion effect is essentially ignored. Acoustic-FFF, acoustic-E-FFF and acoustic-DEP-FFF characterization and separation can also be applied to small particles (down to molecule levels). The above analyses need to be modified to take into account the diffusion effects. For example, Yasuda et al. (1996A) described particle concentration profile in a 1-D ultrasound standing wave and electrical field for particles whose diffusion effects were brought into consideration. For these cases where particle diffusion effects are taken into account, particle equilibrium concentration (or distribution) profile in the vertical direction determines the elution-times of particular particle types. Theoretical analyses for FFF effects of small particles having concentration profiles in the direction normal to the fluid flow were given in many FFF literatures (e.g., Caldwell and Gao, 1993; and Giddings 1993). Those who are skilled in the art, e.g., FFF separation and analysis of molecules and small particles and acoustic/electrophoretic/dielectrophoretic effects of particles, may readily perform theoretical analyses of applying the acoustic-FFF, or acoustic-E-FFF or acoustic-DEP-FFF methods for separating and analyzing molecules and small particles.

REFERENCES

Barmatz MB et al., U.S. Pat. No. 4,523,682, June 1985.
Caldwell K. D. and Gao Y-S., *Anal Chem.* Vol. 65, No. 13, July, 1993, 1764–1772.
Lee S. et al., *Anal. Chem.* Vol. 61, p2439–2444, 1989.
Levin S. and Giddings J. C. *J. Chem. Tech. Biotechnol.*, Vol. 50, p43–56, 1991.
Giddings, *Anal. Chem.* Vol. 53, p 170A–1178A, 1981.
Giddings, *Science*, Vol. 260, p1456–1465, 1993.
Huang Y et al., *Biophys. J* Vol. 73, p1118–1129, 1997.
Huang Y, et al., *J Hematotherapy and Stem Cell Research* Vol. 8, 481–490,1999
Markx, G. H. et al, *J Liq. Chrom. & Rel. Technol.*, Vol. 20, p2857–2872, 1997
Pui P. W. S. et al, *Biotechnol. Prog.* Vol. 11, p146–152, 1995.
Ratanathanawongs S. K. and Giddings J. C. *Anal. Chem.* Vol. 64, p 6–15, 1992
Springston et al, *Anal. Chem.* Vol. 59, p344–350, 1987.
Wang X-B. et al., *Biophys. J* Vol. 74, p2689–2701, 1998.
Williams et al., *Chem. Eng. Comm.* Vol. 111, p121–147, 1992.
Williams et al., *Chem. Eng. Comm.* Vol. 130, p143–166, 1994.
Williams et al., *Chem. Eng. Sci.*, Vol. 51, p4477–4488, 1996.
Williams et al., *Anal Chem.* Vol. 69, p349–360, 1997.

Yang, J. et al. *Anal Chem.* Vol. 71, p911–918, 1999.

Yasuda K. et al, *J Acoust. Soc. Am.* Vol. 99(4), p1965–1970, April, 1996 A.

Yasuda K. et al., *Jpn. J. Appl. Phys.* Vol. 35(1), No. 5B, p3295–3299, 1996 B.

Yasuda K. et al, *J Acoust. Soc. Am.*, Vol. 99(2), p48–1251, 1996 C.

Yasuda K. et at, *J Acoust. Soc. Am.* Vol. 102 (1), p642–645, July, 1997.

Yasuda K. and Kamakura T. *Appl. Phys. Lett*, Vol. 71(13), p1771–1773, September 1997.

Yoshioka K. and Kawashima Y. *Acustica*, Vol. 5, pages 167–173, 1955.

The above examples are included for illustrative purposes only and is not intended to limit the scope of the invention. Since modifications will be apparent to those of skill in this art, it is intended that this invention be limited only by the scope of the appended claims.

What is claimed is:

1. A method of discriminating a matter using electrophoretic and acoustic forces in field flow fractionation, which method comprises:
   a) obtaining an apparatus, which apparatus comprises:
      i) a chamber having at least one inlet port and at least one outlet port said chamber having such structural characteristics that when a carried medium is caused to travel through said chamber, the traveling velocity of said carried medium at various positions within said chamber is different;
      ii) at least two stationary electrode elements adapted along a portion of said chamber, wherein said electrode elements can be energized via at least one electrical signal provided by a first electrical signal generator to create an electrical field, thereby causing at least one electrophoretic force having components normal to the traveling direction of said carrier medium on a matter in said carrier medium; and
      iii) at least one stationary piezoelectric transducer adapted along a portion of said chamber, wherein said piezoelectric transducer can be energized via at least one electrical signal provided by a second electrical signal generator to create an acoustic wave, thereby causing at least one acoustic force having components normal to the traveling direction of said carrier medium on a matter in said carrier medium, wherein said first electrical signal generator and said second electrical signal generator are different electrical signal generators;
   b) introducing a carrier medium containing a matter to be discriminated into the chamber of the apparatus obtained in a) via its inlet port, wherein said introducing causes the carrier medium to travel through the chamber according to a velocity profile;
   c) applying at least one electrical signal provided by a said first electrical signal generator to the electrode elements, wherein said energized electrode elements create an electrical field, thereby causing at least one electrophoretic force on said matter having components normal to the traveling direction of said carrier medium traveling through said chamber; and
   d) applying at least another electrical signal provided by said second electrical signal generator to the piezoelectric transducer, wherein said energized piezoelectric transducer creates an acoustic wave, thereby causing at least one acoustic force on said matter having components normal to the traveling direction of said carrier medium traveling through said chamber, whereby said matter is displaced to positions within said carrier medium along a direction normal to the traveling direction of said carrier medium traveling through said chamber and discriminated according to its position within said carrier medium along the direction normal to the traveling direction of said carrier medium traveling through said chamber.

2. The method of claim 1, wherein the electrophoretic force and the acoustic force are generated simultaneously.

3. The method of claim 1, wherein the electrophoretic force and the acoustic force are generated sequentially.

4. The method of claim 1, wherein the apparatus comprises more than two electrode elements.

5. The method of claim 1, wherein each of more than two electrode elements in the apparatus is individually connected to one of a plurality of electrical conductor buses electrically connected to the electrical signal generator.

6. The method of claim 1, wherein the electrode elements in the apparatus are adapted substantially longitudinally or latitudinally along a portion of the chamber.

7. The method of claim 1, wherein the electrode elements in the apparatus are adapted along the interior surface of the chamber.

8. The method of claim 1, wherein the electrode elements in the apparatus are configured on a plane substantially parallel to the traveling direction of carrier medium caused to travel through said chamber.

9. The method of claim 1, wherein the electrode elements in the apparatus form an electrode array, said electrode array Is selected from an interdigitated electrode array, interdigitated castellated electrode array, interdigitated electrode array having periodic triangular shaped tips on the electrode elements, interdigitated electrode array having periodic arc shaped tips on the electrode elements.

10. The method of claim 1, wherein the electrode elements in the apparatus are a metal layer coated on a surface of the chamber.

11. The method of claim 10, wherein the metal is selected from a group of gold, platinum, aluminum, chromium, titanium, copper and silver.

12. The method of claim 1, wherein the first electrical signal generator in the apparatus for energizing the electrode elements to create the electrophoretic force is a DC signal source capable of varying magnitude of DC voltage, or is a AC signal source capable of varying magnitude and frequency, of said electrical signals.

13. The method of claim 1, wherein file first electrical signal in the apparatus for energizing the electrode elements to create the electrophoretic force is a DC electrical signal or a low frequency AC signal.

14. The method of claim 1, wherein the chamber comprises a tube.

15. The method of claim 14, wherein the electrode elements and/or the piezoelectric transducer, or a plurality thereof, are adapted along the interior surface of the tube.

16. The method of claim 14, wherein the electrode elements and/or the piezoelectric transducer, or a plurality thereof, are adapted along the exterior surface of the tube.

17. The method of claim 1, wherein the chamber comprises a top wall, a bottom wall, and two side walls and the electrode elements and/or the piezoelectric transducer, or a plurality thereof, are configured on the top wall of the chamber.

18. The method of claim 1, wherein the chamber comprises a top wall, a bottom wall, and two side walls and the electrode elements and/or the piezoelectric transducer, or a plurality thereof, are configured on the bottom wall of the chamber.

19. The method of claim 1, wherein file electrode elements and/or the piezoelectric transducer, or a plurality thereof, is adapted on opposing surfaces of the chamber.

20. A method of discriminating a matter using electrophoretic and acoustic forces in field flow fractionation, which method comprises:
  a) obtaining an apparatus, which apparatus comprises:
    i) a chamber having at least one inlet port and at least one outlet port, said chamber having such structural characteristics that when a carried medium is caused to travel through said chamber, the traveling velocity of said carried medium at various positions within said chamber is different;
    ii) at least two stationary electrode elements adapted along a portion of said chamber, wherein said electrode elements can be energized via at least one electrical signal provided by a first electrical signal generator to create an electrical field, thereby causing at least one electrophoretic force having components normal to the traveling direction of said carrier medium on a matter in said carrier medium; and
    iii) at least one stationary piezoelectric transducer adapted along a portion of said chamber, wherein said piezoelectric transducer can be energized via at least one electrical signal provided by a second electrical signal generator to create an acoustic wave, thereby causing at least one acoustic force having components normal to the traveling direction of said carrier medium on a matter in said carrier medium, wherein said first electrical signal generator and said second electrical signal generator are different electrical signal generators;
  b) loading a carrier medium into the chamber of apparatus obtained in a) via its inlet port until the chamber is filled with the carrier medium;
  c) delivering a sample that contains a matter to be discriminated into the carrier medium in the chamber;
  d) applying at least one electrical signal provided by said first electrical signal generator to the electrode elements, wherein said energized electrode elements create an electrical field, thereby causing at least one electrophoretic force on said matter;
  e) applying at least another electrical signal provided by said second electrical signal generator to the piezoelectric transducer, wherein said energized piezoelectric transducer creates an acoustic wave, thereby causing at least one acoustic force on said matter;
  f) introducing the carrier medium into the chamber of the apparatus via its inlet port, wherein said introducing causes the carrier medium to travel through the chamber according to a velocity profile,
  whereby said matter is displaced to positions within said carrier medium along a direction normal to the traveling direction of said carrier medium traveling through said chamber and discriminated according to its position within said carrier medium along the direction normal to the traveling direction of said carrier medium traveling through said chamber.

21. The method of claim 20, wherein applying electrical signal to the electrode elements to cause at least one electrophoretic force on said matter and applying electrical signal to the piezoelectric transducer to cause at least one acoustic force on said matter result in the matter being displaced into equilibrium position along a direction normal to the traveling direction of the carrier medium traveling through the chamber, prior to the introducing of carrier medium into the chamber that causes the carrier medium to travel through the chamber according to a velocity profile.

22. The method of claim 20, wherein the electrophoretic force and the acoustic force are generated simultaneously.

23. The method of claim 20, wherein the electrophoretic force and the acoustic force are generated sequentially.

24. A method of discriminating a matter using dielectrophoretic and acoustic forces in field flow fractionation, which method comprises:
  a) obtaining an apparatus, which apparatus comprises:
    i) a chamber having at least one inlet port and at least one outlet port, said chamber having such structural characteristics that when a carried medium is caused to travel through said chamber, the traveling velocity of said carried medium at various positions within said chamber is different;
    ii) at least two stationary electrode elements adapted along a portion of said chamber, wherein said electrode elements can be energized via at least one electrical signal provided by a first electrical signal generator to create a non-uniform electrical field, thereby causing at least one dielectrophoretic force having components normal to the traveling direction of said carrier medium on a matter in said carrier medium; and
    iii) at least one stationary piezoelectric transducer adapted along a portion of said chamber, wherein said piezoelectric transducer can be energized via at least one electrical signal provided by a second electrical signal generator to create an acoustic wave, thereby causing at least one acoustic force having components normal to the traveling direction of said carrier medium on a matter in said carrier medium, wherein said first electrical signal generator and said second electrical signal generator are different electrical signal generators;
  b) introducing a carrier medium containing a matter to be discriminated into the chamber of the apparatus obtained in a) via its inlet port, wherein said introducing causes the carrier medium to travel through the chamber according to a velocity profile;
  c) applying at least one electrical signal provided by said first electrical signal generator to the electrode elements, wherein said energized electrode elements create a non-uniform electrical field, thereby causing at least one dielectrophoretic force on said matter having components normal to the traveling direction of said carrier medium traveling through said chamber; and
  d) applying at least another electrical signal provided by said second electrical signal generator to the piezoelectric transducer, wherein said energized piezoelectric transducer creates an acoustic wave, thereby causing at least one acoustic force on said matter having components normal to the traveling direction of said carrier medium traveling through said chamber,
  whereby said matter is displaced to positions within said carrier medium along a direction normal to the traveling direction of said carrier medium traveling through said chamber and discriminated according to its position within said carrier medium along the direction normal to the traveling direction of said carrier medium traveling through said chamber.

25. The method of claim 24, wherein the dielectrophoretic force and the acoustic force are generated simultaneously.

26. The method of claim 24, wherein the dielectrophoretic force and the acoustic force are generated sequentially.

27. The method of claim 24, wherein the apparatus comprises more than two electrode elements.

28. The method of claim 24, wherein each of more than two electrode elements in the apparatus is individually connected to one of a plurality of electrical conductor buses electrically connected to the electrical signal generator.

29. The method of claim 24, wherein the electrode elements in the apparatus further creates a spatially inhomogeneous electric field.

30. The method of claim 24, wherein the first electrical signal generator in the apparatus for energizing the electrode elements to create the dielectrophoretic force is capable of varying magnitude, and frequency of said electrical signals.

31. A method of discriminating a matter using dielectrophoretic and acoustic forces in field flow fractionation, which method comprises:
   a) obtaining an apparatus, which apparatus comprises:
      i) a chamber having at least one inlet port and at least one outlet port, said chamber having such structural characteristics that when a carried medium is caused to travel through said chamber, the traveling velocity of said carried medium at various positions within said chamber is different;
      ii) at least two stationary electrode elements adapted along a portion of said chamber, wherein said electrode elements can be energized via at least one electrical signal provided by a first electrical signal generator to create a non-uniform electrical field, thereby causing at least one dielectrophoretic force having components normal to the traveling direction of said carrier medium on a matter in said carrier medium; and
      iii) at least one stationary piezoelectric transducer adapted along a portion of said chamber, wherein said piezoelectric transducer can be energized via at least one electrical signal provided by a second electrical signal generator to create an acoustic wave, thereby causing at least one acoustic force having components normal to the traveling direction of said carrier medium on a matter in said carrier medium, wherein said first electrical signal generator and said second electrical signal generator are different electrical signal generators;
   b) loading a carrier medium into the chamber of the apparatus obtained in a) via its inlet port until the chamber is filled with the carrier medium;
   c) delivering a sample that contains a matter to be discriminated into the carrier medium in the chamber;
   d) applying at least one electrical signal provided by said first electrical signal generator to the electrode elements, wherein said energized electrode elements create an electrical field, thereby causing at least one dielectrophoretic force on said matter;
   e) applying at least another electrical signal provided by said second electrical signal generator to the piezoelectric transducer, wherein said energized piezoelectric transducer creates an acoustic wave, thereby causing at least one acoustic force on said matter;
   f) introducing the carrier medium into the chamber of the apparatus via its inlet port, wherein said introducing causes the carrier medium to travel through the chamber according to a velocity profile,
   whereby said matter is displaced to positions within said carrier medium along a direction normal to the traveling direction of said carrier medium traveling through said chamber and discriminated according to its position within said carrier medium along the direction normal to the traveling direction of said carrier medium traveling through said chamber.

32. The method of claim 31, wherein applying electrical signal to the electrode elements to cause dielectrophoretic force on said matter and applying electrical signal to the piezoelectric transducer to cause acoustic force on said matter result in the matter being displaced into equilibrium position along a direction normal to the traveling direction of the carrier medium traveling through the chamber, prior to the introducing of carrier medium into the chamber that causes the carrier medium to travel through the chamber according to a velocity profile.

33. The method of claim 31, wherein the dielectrophoretic force and the acoustic force are generated simultaneously.

34. The method of claim 31, wherein the dielectrophoretic force and the acoustic force are generated sequentially.

* * * * *